(12) United States Patent
Kinoshita et al.

(10) Patent No.: US 8,187,206 B2
(45) Date of Patent: May 29, 2012

(54) GUIDE WIRE

(75) Inventors: Yasushi Kinoshita, Fujinomiya (JP);
Junichi Kobayashi, Fujinomiya (JP);
Tadashi Kousai, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 87 days.

(21) Appl. No.: 12/048,664

(22) Filed: Mar. 14, 2008

(65) Prior Publication Data

US 2008/0228109 A1    Sep. 18, 2008

(30) Foreign Application Priority Data

Mar. 14, 2007  (JP) .................................. 2007-65890
Mar. 23, 2007  (JP) .................................. 2007-77917
Jan. 18, 2008  (JP) .................................. 2008-009726

(51) Int. Cl.
*A61B 5/00* (2006.01)
*A61M 25/00* (2006.01)

(52) U.S. Cl. ...................................... 600/585

(58) Field of Classification Search ................... 600/585
See application file for complete search history.

(56) References Cited

U.S. PATENT DOCUMENTS

| | | | |
|---|---|---|---|
| 5,084,022 A | | 1/1992 | Claude |
| 5,379,779 A | | 1/1995 | Rowland et al. |
| 5,404,887 A | * | 4/1995 | Prather .......................... 600/585 |
| 5,479,938 A | | 1/1996 | Weier |
| 5,756,144 A | * | 5/1998 | Wolff et al. ..................... 427/2.3 |
| 5,824,049 A | * | 10/1998 | Ragheb et al. ................. 623/1.44 |
| 5,827,201 A | * | 10/1998 | Samson et al. .................. 600/585 |
| 6,251,085 B1 | * | 6/2001 | Tezuka ............................ 600/585 |
| 6,340,441 B1 | * | 1/2002 | Meyer et al. ............. 264/173.12 |
| 6,494,847 B1 | * | 12/2002 | Richardson et al. ........... 600/585 |
| 6,591,472 B1 | * | 7/2003 | Noone et al. ..................... 29/417 |
| 6,786,876 B2 | * | 9/2004 | Cox ................................ 600/585 |
| 6,811,958 B2 | | 11/2004 | Iwami et al. |
| 7,651,469 B2 | * | 1/2010 | Osborne et al. ................ 600/585 |
| 7,687,144 B2 | * | 3/2010 | Clark et al. .................... 428/383 |
| 2003/0229298 A1 | * | 12/2003 | Iwami et al. ................... 600/585 |
| 2004/0167439 A1 | * | 8/2004 | Sharrow ......................... 600/585 |

(Continued)

FOREIGN PATENT DOCUMENTS

DE    198 29 620 A1    2/1999

(Continued)

OTHER PUBLICATIONS

Extended European Search Report issued Jul. 17, 2008 in corresponding EP Patent Appln. No. 08 10 2452, EPO, Berlin, DE.

(Continued)

*Primary Examiner* — Max Hindenburg
*Assistant Examiner* — Devin Henson
(74) *Attorney, Agent, or Firm* — Buchanan Ingersoll & Rooney PC

(57) ABSTRACT

A guide wire includes a member with a core wire. The guide wire may have a marker-forming layer which partly encircles the outer surface of the member and differs in color from the member, and a coating layer which covers the marker-forming layer and the member at least in the region where the marker-forming layer is formed and has such transparency as to make the marker-forming layer visible. The marker-forming layer and the coating layer can be formed from mutually miscible resins, while the marker-forming layer functions as a visible marker.

24 Claims, 15 Drawing Sheets

U.S. PATENT DOCUMENTS

| | | | |
|---|---|---|---|
| 2006/0047224 A1* | 3/2006 | Grandfield | 600/585 |
| 2006/0073264 A1* | 4/2006 | Sakane et al. | 427/2.1 |
| 2006/0116609 A1 | 6/2006 | Kanuka et al. | |
| 2006/0211952 A1* | 9/2006 | Kennedy, II | 600/585 |

FOREIGN PATENT DOCUMENTS

| | | |
|---|---|---|
| EP | 0 771 572 A1 | 5/1997 |
| EP | 1 203 595 A1 | 5/2002 |
| EP | 1 348 461 A2 | 10/2003 |
| EP | 1 348 461 A3 | 10/2003 |
| JP | 2001-046508 A | 2/2001 |
| WO | WO 00/74565 A1 | 12/2000 |

OTHER PUBLICATIONS

Extended European Search Report issued Aug. 19, 2009 by European Patent Office in a corresponding European Patent Application.

* cited by examiner

GUIDE WIRE

TECHNICAL FIELD

The present invention relates to a guide wire. More particularly, the present invention relates to a guide wire (or a transendoscopic guide wire) to be inserted into a living organism through an endoscope.

BACKGROUND DISCUSSION

A guide wire is used to facilitate insertion of a catheter into a lumen (such as digestive tract and blood vessel) of a living body. It leads a catheter slipped thereon to a desired position in a lumen.

A guide wire is also used to lead a catheter to a desired position in a lumen of a living body through an endoscope or a lumen of an endoscope at the time of observation or treatment of a lumen of a living body.

A guide wire for this purpose has a marker on its surface which tells its position and movement during insertion. A guide wire in a single color without a marker cannot be recognized for its movement when it turns around its axis. There have been proposed several methods for attaching a marker to a guide wire.

One method is described in U.S. Pat. No. 5,379,779 and involves slipping a hollow tube of polytetrafluoroethylene (PTFE), having one or more colored spiral pattern, onto a core wire and subsequently allowing it to be heat-shrink around the core wire of a guide wire.

Another method described in U.S. Pat. No. 6,811,958 involves adding a color producing agent (such as mica which produces a color upon irradiation with a laser beam) to the covering layer on the core of the guide wire and irradiating the covering layer with a laser beam for color development, thereby forming a marker as desired.

The above-mentioned guide wires include those which have surface irregularities formed thereon.

An example is disclosed in U.S. Patent Application Publication No. 2006/116609 in which the guide wire has a curved part on which surface irregularities are formed so as to make it more flexible. This guide wire has its surface irregularities formed from the outermost layer which is partly removed by heating a coil wound around the curved part at prescribed intervals.

SUMMARY

A guide wire includes a member with a core wire. According to one aspect, the guide wire may include a bulge-forming layer partially arranged on the outer surface of the member, and a coating layer to cover said bulge-forming layer and said member at least in the region where the bulge-forming layer is arranged, the guide wire having its outer surface shaped such that the part where the bulge-forming layer is arranged bulges relative to the part where the bulge-forming layer is not arranged.

The bulge-forming layer may be arranged in the region where the coating layer covering the part without the bulge-forming layer lies immediately on a surface having minute irregularities. The bulge-forming layer preferably has a color different from that of the member, the coating layer has such transparency as to make the bulge-forming layer visible, and the bulge-forming is so arranged as to function as a visible marker.

According to another aspect, the guide wire may include an undercoating layer formed at least on part of the outer surface of the member, a bulge-forming layer partially arranged on the outer surface of the undercoating layer, and a coating layer to cover the bulge-forming layer and the member at least in the region where the bulge-forming layer is arranged, the guide wire having its outer surface shaped such that the part where the bulge-forming layer is arranged bulges relative to the part where the bulge-forming layer is not arranged, wherein the bulge-forming layer and the undercoating layer are made of materials containing mutually miscible resins.

The bulge-forming layer preferably has a color different from that of the undercoating layer and the coating layer has such transparency as to make the bulge-forming layer visible, so that the bulge-forming layer functions as a visible marker.

The coating layer firmly may adhere to the undercoating layer in the region where the bulge-forming layer is not arranged.

The bulge-forming layer preferably is in a spiral, circular, or check pattern.

According to further aspect, the guide wire may include a bulge-forming layer which covers the outer surface of the member and bulges partly from the outer surface, and a coating layer to cover the bulge-forming layer, the guide wire having its outer surface shaped such that the part corresponding to the bulge of the bulge-forming layer bulges relative to the part not corresponding to the bulge of the bulge-forming layer, wherein the bulge-forming layer and the coating layer are formed from materials containing mutually miscible resins.

According to more aspect, the guide wire may include a marker-forming layer which partly encircles the outer surface of the member and differs in color from the member, and a coating layer which covers the marker-forming layer and the member at least in the region where the marker-forming layer is formed and has such transparency as to make the marker-forming layer visible, the marker-forming layer and the coating layer being formed from mutually miscible resins, and the marker-forming layer functioning as a visible marker.

The marker-forming layer may be composed of a first resin, a second resin differing from the first resin, and a pigment, and the coating layer is composed of a material containing the second resin.

The guide wire may further include an outer layer which covers the coating layer and has such transparency as to make the marker-forming layer visible, the outer layer and the coating layer being composed of materials containing a resin common to them.

The guide wire may further include an undercoating layer which covers the outer surface of the member at least in the region where the marker-forming layer is formed and an intermediate layer which covers the undercoating layer, the marker-forming layer being formed partly on the intermediate layer, the intermediate later being composed of a material containing the first resin, and the undercoating layer being composed of a material containing a resin miscible with the first resin.

The marker-forming layer may be composed of a material containing a second resin differing from the first resin and a pigment, and the coating layer is composed of a material containing a resin which is different from the first resin and miscible with the second resin.

BRIEF DESCRIPTION OF THE DRAWING FIGURES

DETAILED DESCRIPTION

Figure 1:
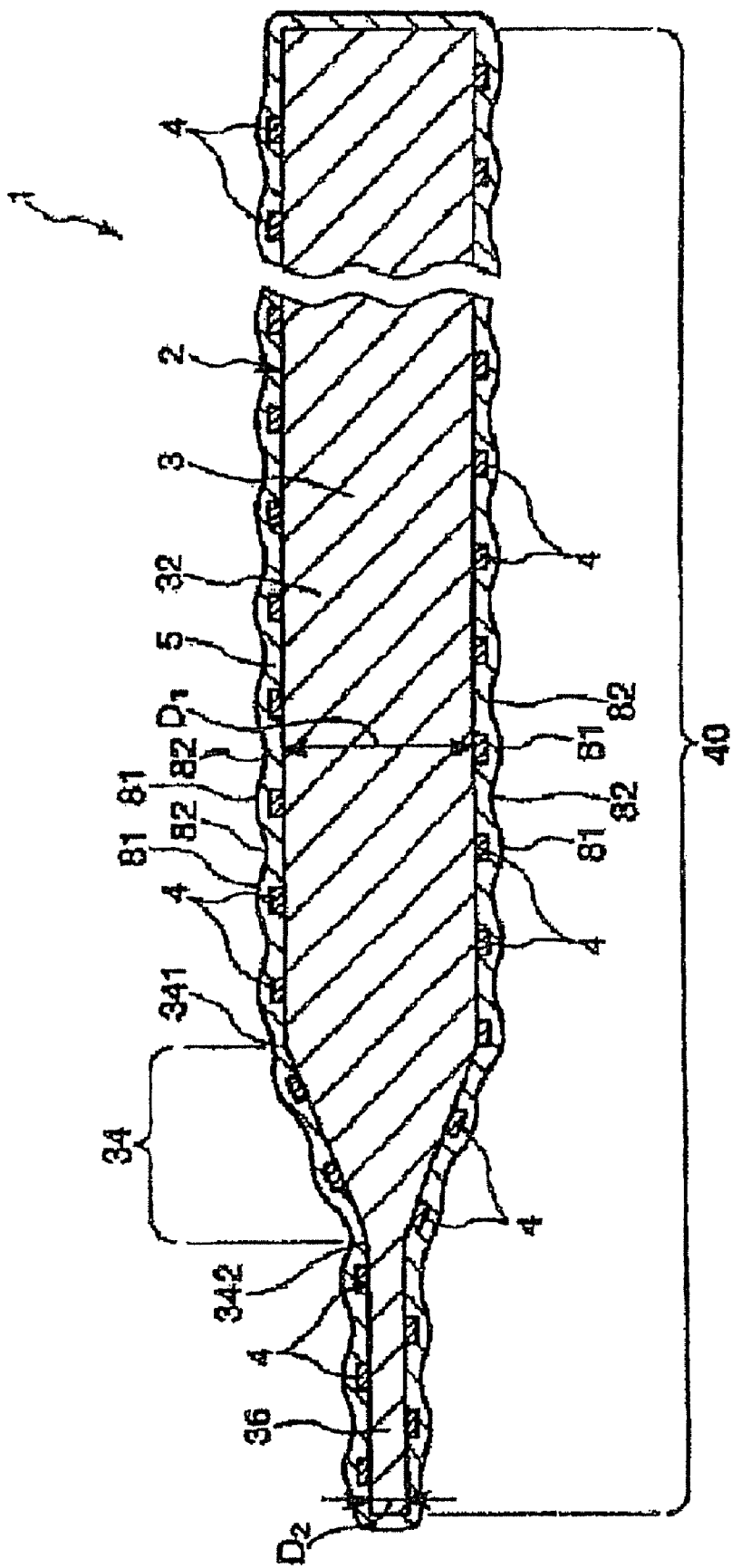
FIG. 1 is a longitudinal cross-sectional view of a first embodiment of the guide wire disclosed here.
Figure 2:
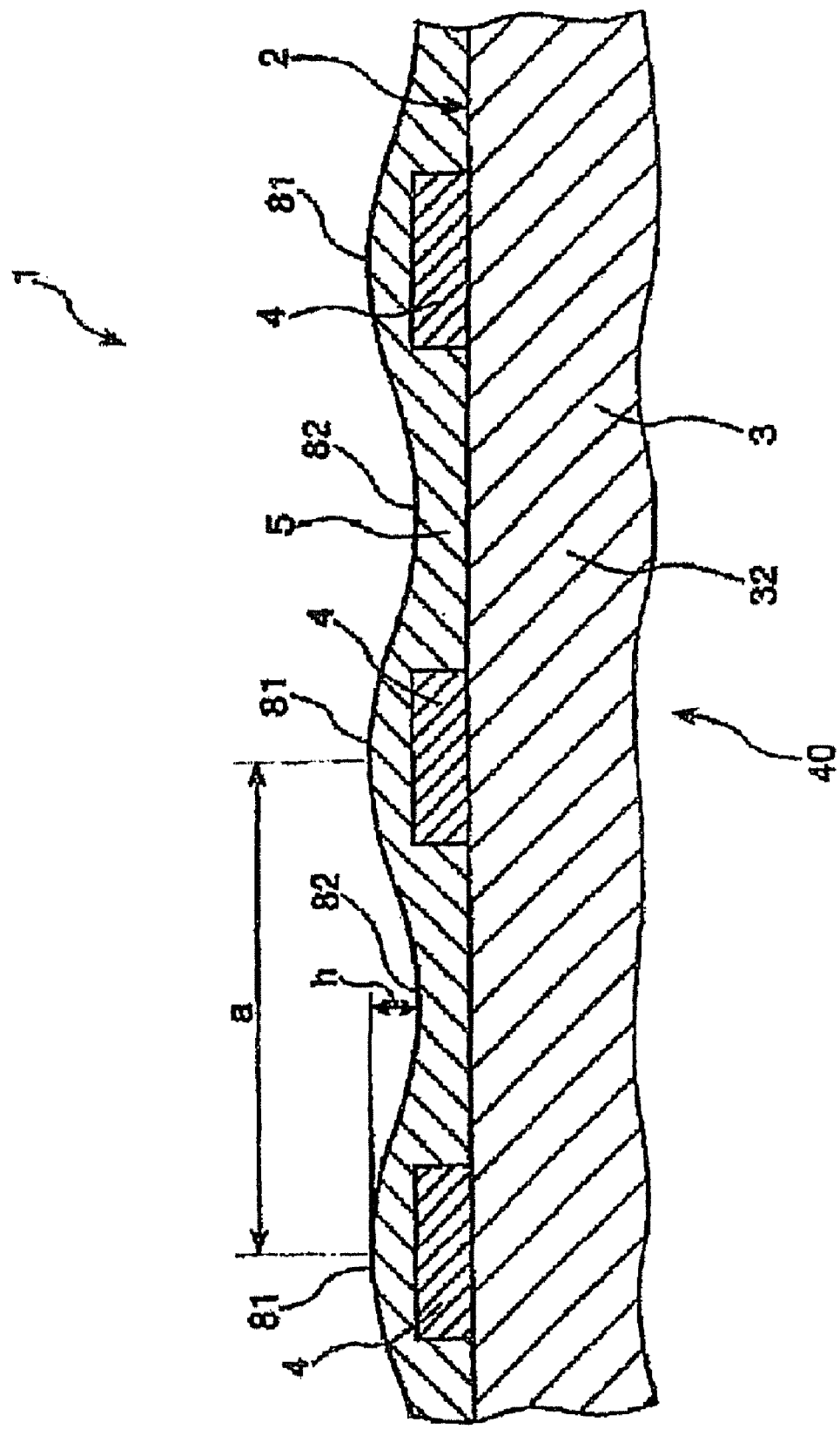
FIG. 2 is a partial longitudinal cross-sectional view of the part of the FIG. 1 guide wire near the outer surface of the guide wire.

FIGS. 1 and 2 illustrate a guide wire according to one disclosed embodiment. It is to be understood that the guide wire is illustrated in FIG. 1 in a manner intended to facilitate an understanding of the guide wire, and so the guide wire is depicted with its length shortened and its thickness exaggerated. Therefore, the illustration is different from actual in the ratio of thickness to length. For the sake of convenience in description, the right and left sides in FIG. 1 are designated as "base end" and "forward end," respectively.

As shown in FIG. 1, the guide wire 1 includes a member 2, a bulge-forming layer 4, and a coating layer 5. The member 2 is a flexible core wire 3. The bulge-forming layer 4 differs in color from the member 2 (core wire 3) and results in the outer surface of the guide wire 1 possessing a bulge. The coating layer 5 possesses a transparency (light transmission) which makes the bulge-forming layer 4 visible.

According to this embodiment, the member 2 is a single continuous core wire 3 and has a round cross-section. However, the member 2 may be composed of two or more different or identical core wires joined together by welding or brazing. It may also have any additional structure.

The guide wire 1 is not specifically restricted in its overall length. A preferred overall length is about 200 to 5,000 mm. Also, the guide wire is not specifically restricted in outside diameter. A preferred outside diameter is about 0.2 to 1.2 mm.

The core wire 3 extends over the entire length of the guide wire 1. The core wire includes a main part 32 (which corresponds to the main body of the guide wire 1), a tapered part 34 (which is close to the forward end, closer to the forward end than the rearward end), and a relatively thin part 36 (at the forward end). The main part 32 has a nearly constant outside diameter. The tapered part 34 gradually decreases in outside diameter toward the forward end. The relatively thin part 36 has a nearly constant outside diameter.

The tapered part 34 results in the core wire 3 gradually (continuously in the illustrated embodiment) increasing in flexibility in a direction from the boundary (or the base end 341 of the tapered part) between the main part 32 and the tapered part 34 toward the forward end. This adds flexibility to the guide wire 1, thereby making it relatively easy and safe to insert the guide wire 1 into a living body.

The relatively thin part 36 extends from the tapered part 34 to the forward end of the guide wire and is more flexible than the rest of the guide wire.

The main part 32 of the core wire 3 has an outside diameter D1 (measured at the base end 341 of the tapered part), which is not specifically restricted but should preferably be about 0.3 to 1.0 mm, more preferably about 0.4 to 0.7 mm.

The relatively thin part 36 of the core wire 3 has an outside diameter D2 (measured at the forward end 342 of the tapered part), which is not specifically restricted but should preferably be about 0.05 to 0.3 mm, more preferably about 0.1 to 0.2 mm. The outside diameter of the relatively thin part 36 may be constant or may gradually decrease in a direction toward the forward end.

The length of the tapered part 34 may vary depending on the use of the guide wire and the kind of guide wire. Though not limited in this regard, the length of the tapered part 34 should preferably be about 10 to 300 mm, more preferably about 30 to 250 mm.

The length of the relatively thin part 36 is also not specifically restricted. Nevertheless, it should preferably be about 0 to 100 mm, more preferably about 10 to 50 mm.

The outside diameter of the tapered part 34 may decrease at a constant rate or a varying rate along the lengthwise direction of the core wire 3 (the member 2). Also, there may be two or more of the tapered part 34.

The core wire 3 should preferably have minute surface irregularities. This is true particularly for that part of the outer surface (immediately under the coating layer 5) where the bulge-forming layer 4 in the bulge-forming region 40 (mentioned later) is not yet formed. The minute surface irregularities (which are sufficiently small compared with the bulging part 81 and recessed part 82 mentioned later) improve adhesion between the core wire 3 and the coating layer 5, thereby inhibiting or preferably preventing the coating layer 5 from peeling off.

The core wire 3 may be made of metallic materials, such as stainless steel, Ni—Ti alloy, Ni—Al alloy, Cu—Zn alloy, and other superelastic alloys, or resin materials having a comparatively high stiffness. They may be used alone or in combination with one another.

The guide wire 1 disclosed here is not specifically restricted in its application. It may be used, for example, to guide a catheter to a desired position (such as a cavity in a living body) through the lumen of an endoscope. A guide wire used in this manner is referred to as a "transendoscopic guide wire." The embodiment mentioned below is concerned typically with the case in which the guide wire 1 is used as a transendoscopic guide wire.

The transendoscopic guide wire has a visible marker on its outer surface, so that the marker is visible through the endoscope. In this embodiment, the bulge-forming layer 4 functions not only as a means for causing the outer surface of the guide wire 1 to partly bulge (or means for arranging both the bulging part 81 and the recessed part 82) but also as the visible marker. The outer surface of the guide wire 1 has a plurality of bulging parts and non-bulging parts.

As mentioned, the guide wire 1 includes the bulge-forming region 40 in which the bulge-forming layer 4 is formed. On the outer layer of the core wire 3 (or the member 2) in the bulge-forming region 40 is a portion of the bulge-forming layer 4. The bulge-forming layer 4 differs in color from the outer surface of the core wire 3 (or the member 2), so that it functions as the visible marker or a marker layer.

The bulge-forming region 40 may extend entirely or partly (along the overall length) in the lengthwise direction of the core wire 3. In this embodiment, the bulge-forming region 40 extends over the entire length of the core wire 3 from the proximal end of the core wire 3o the distal end of the core wire 3.

The bulge-forming region 40, which is formed on at least a part of the core wire 3, should at least extend from the forward end of the core wire 3 to the midway of the core wire 3. The length of the bulge-forming region 40 in the lengthwise direction should preferably be 5 cm or longer, more preferably about 10 to 50 cm, most preferably about 20 to 40 cm.

The bulge-forming layer 4 may be formed from a material containing a resin and a pigment. The color of the bulge-forming layer 4 depends mainly on the kind, amount, and properties of the pigment contained therein and also on the composition and properties (especially color) of the resin material contained therein. Any color can be produced by an adequate or appropriate combination.

The color of the bulge-forming layer 4 is important so that the operator can observe the movement of the guide wire 1 through the endoscope. An adequate color should be selected in view of the color of the core wire 3 (or the member 2) underneath.

To cite an example, the core 3 or its oxide coating film may have a silver white color (metallic color) or a grayish or black color, and the bulge-forming layer 4 may have a reddish or yellowish color. In this case there is a large difference in brightness between them, which gives rise to a high contract. Thus the bulge-forming layer 4 is highly visible, which is desirable. Another case in which they have complementary colors is also desirable because of the high visibility of the bulge-forming layer 4. A high contrast is obtained when a dark color such as black (or other dark colors such as charcoal gray, dark brown, navy blue, and violet) is combined with a light color (such as yellow, yellowish green, and orange), or when blue is combined with red, orange, or pink. A high contrast is also obtained by a combination of the same colors differing in shade, such as dark blue with light blue and reddish-brown with pink.

The constituent material of the bulge-forming layer 4 preferably contain any one of resins (1) and (2) listed below.

(1) Heat-Resistant Resins Which Have a Melting Point of 200° C. or Higher, Preferably About 200 to 300° C.

Examples of the heat-resistant resins include polysulfone, polyimide, polyether-ether ketone, polyarylene ketone, polyphenylenesulfide, polyarylenesulfide, polyamideimide, polyetherimide, polyimidesulfone, polyarylsulfone, polyarylethersulfone, polyester, polyethersulfone, and fluororesin, such as polytetrafluoroethylene (PTFE) and ethylene-tetrafluoroethylene copolymer (ETFE). They may be used alone or in combination with one another.

(2) Thermosetting Resins

Examples of the thermosetting resins include epoxy resin, phenolic resin, unsaturated polyester resin, polyimide resin, silicone resin, and polyurethane resin. They may be used alone or in combination with one another. The bulge-forming layer 4 as a whole should contain pigment in an amount of about 10 to 99 wt %, preferably about 50 to 95 wt %, to produce desired colors. An adequate amount depends on the type and properties of the pigment and the composition and properties of the resin material. The bulge-forming layer 4 should preferably contain pigment uniformly distributed therein, although uneven distribution in its outer surface is permissible.

Pigments may be used alone or in combination with one another in the form of a mixture.

The bulge-forming layer 4 is not specifically restricted in shape (pattern) and dimensions. It depends on the shape (pattern) of the bulging part 81 and the recessed part 82 to be formed. However, it should preferably have a thickness of about 1 to 30 µm, more preferably about 2 to 10 µm, so that the guide wire 1 can be made relatively thin.

As shown in the figure, the bulge-forming layer 4 takes on a spiral pattern. The spiral (or circular) pattern should preferably have a width (i.e., the width of the bulge-forming layer 4) of about 0.3 to 10 mm and a pitch (gap) of about 0.5 to 10 mm.

The shape of the bulge-forming layer 4 is not restricted to spiral or circular. Any shape is acceptable so long as it is visible if the bulge-forming layer is to function as a visible marker. It may be a continuous line with a visible width or a discontinuous pattern with a visible area. It includes, for example, straight line, wavy pattern, polka dots, check pattern, and mesh pattern. It also includes numerals, letters, symbols, and graduations, which are visible. Two or more different patterns may be combined with each other (for example, a spiral pattern and a circular pattern placed on top of the other) for better visibility.

The pigment may be either an inorganic pigment(s) or an organic pigment(s), with the former being preferable because of their good heat resistance. Inorganic pigments include carbon black, mica, titanium dioxide, nickel-titanium yellow, prussian blue, milori blue, cobalt blue, ultramarine, and viridian blue.

The coating layer 5 has such transparency as to make the bulge-forming layer 4 visible. It covers the bulge-forming layer 4 and the core wire 3 (or the member 2) in at least the bulge-forming region 40. In this embodiment, the coating layer 5 covers the bulge-forming layer 4 and the entire length of the core wire 3.

The outer surface of the coating layer 5 (or the outer surface of the guide wire 1) has the part where the bulge-forming layer 4 is formed and the part where the bulge-forming layer 4 is not formed, the former bulging relative to the latter. In other words, the part where the bulge-forming layer 4 is formed is the bulging part 81, and the part where the bulge-forming layer 4 is not formed is the recessed part 82. Since the coating layer 5 is comparatively thin, the outer surface of the coating layer 5 bulges in conformity with the shape and pattern of the bulge-forming layer 4.

This structure reduces the area of contact between the outer surface of the coating layer 5 and the lumen of the catheter or the lumen of the endoscope, and also reduces frictional resistance (or sliding resistance), thereby improving the operability of the guide wire 1.

The bulging part 81 and the recessed part 82 are not formed by directly fabricating the coating layer 5, but they result from the bulge-forming layer 4 immediately under the coating layer 5. Therefore, the outer surface of the coating layer 5 is smooth without sharp angles and projections. In other words, the bulging part 81 and the recessed part 82 have their corners rounded. This structure improves slidability and contributes to higher safety.

The bulging part 81 and the recessed part 82 are not specifically restricted in shape and pattern. However, in the illustrated structure, the bulging part 81 possesses a spiral pattern.

In the case where the bulging part 81 and the recessed part 82 in spiral or circular pattern are formed alternately along the lengthwise direction of the core wire 3 (member 2), they should be separated from each other at intervals (a) of about 0.5 to 10 mm, preferably about 1 to 5 mm.

The bulging part 81 should have an average height (h) of about 1 to 30 μm, preferably 2 to 10 μm.

The coating layer 5 is formed from a resin-containing material.

The constituent material of the coating layer 5 may contain any resin which is not specifically restricted. At least one of the resins should be the one which is miscible with the resin contained in the constituent material of the bulge-forming layer 4. In other words, mutually miscible resins should be contained in the constituent material for the coating layer 5 and the constituent material for the bulge-forming layer 4. This ensures firm adhesion between the bulge-forming layer 4 and the coating layer 5, thereby preventing the coating layer 5 from peeling off even when the guide wire 1 experiences repeated bending and twisting.

"Miscibility" means that the two components are able to well dissolve each other thermodynamically. In other words, they do not separate from each other after curing.

Mutually miscible resins may be the same resins or different resins. Examples of combinations of different resins include polyamideimide and polyimide, polyetherimide and polyimide, polyamideimide and polyetherimide, or polysulfone and polyethersulfone, which have common groups, such as imide and sulfone.

The content of the mutually miscible resins in the bulge-forming layer 4 should preferably be about 1 to 90 wt %, more preferably about 5 to 50 wt %, based on the total weight of the bulge-forming layer 4, for good adhesion between the bulge-forming layer 4 and the coating layer 5. The content of the mutually miscible resins in the coating layer 5 should preferably be about 1 to 50 wt %, more preferably about 3 to 35 wt %, based on the total weight of the coating layer 5, for good adhesion between the bulge-forming layer 4 and the coating layer 5.

The coating layer 5 is not specifically restricted in thickness. It should preferably have a thickness of about 1 to 20 μm, more preferably about 2 to 10 μm, depending on the dimensions of the bulging part 81 and the recessed part 82.

The total thickness of the coating layer 5 and the bulge-forming layer 4 at the bulging part 81 is not specifically restricted; it should be 50 μm or smaller, preferably about 2 to 40 μm, more preferably about 4 to 20 μm.

The foregoing thickness is necessary for the guide 1 to have a small diameter. This object is not achieved with the conventional visible marker, which is formed by covering the core wire with a heat-shrinkable tube (as thick as about 100 μm) having a spiral or parallel stripy pattern. In this embodiment, the bulge-forming layer 4 and the coating layer 5 having the foregoing thickness can be formed relatively easily and certainly by using the structure (mentioned above) and the production method (mentioned later).

The method for producing the guide wire 1 is not described in detail here, but will be described later together with the method for producing the guide wire 1 according to the second embodiment.

As mentioned above, the guide wire 1 according to the first embodiment has the bulged part 81 and the recessed part 82 formed on the outer surface of the guide wire. As mentioned, this structure reduces the area of contact between the outer surface of the coating layer 5 and the inside of the catheter or the lumen of the endoscope, and also reduces frictional resistance (or sliding resistance), thereby improving the operability of the guide wire 1.

The bulging part 81 and the recessed part 82 are not formed by directly fabricating the coating layer 5, but result from the bulge-forming layer 4 located immediately under the coating layer 5. Therefore, the outer surface of the coating layer 5 is smooth without sharp angles and projections. In other words, the bulging part 81 and the recessed part 82 have their corners rounded. This structure helps improve slidability and contribute to higher safety.

The guide wire 1 according to the first embodiment has a relatively small diameter, and the bulge-forming layer 4 has any desired color owing to adequate selection of pigment and resin material (for composition and amount) contained therein. The bulge-forming layer 4 allows a wide selection of colors for any color of the core wire 3 (or the member 2). Therefore, the resulting guide wire 1 has an easily visible marker.

Since the coating layer 5 and the bulge-forming layer 4 are formed from mutually miscible resins, they firmly adhere to each other and the coating layer 5 remains without peeling off even when the guide wire 1 experiences bending and twisting repeatedly.

According to this embodiment, the bulge-forming layer 4 may not function as a visible marker. In this case the bulge-forming layer 4 is not required to contain any pigment. In other words, the bulge-forming layer 4 may have the same color as the core wire 3 (or the member 2), or it may be transparent or opaque. In addition, the coating layer 5 may also be transparent, and the bulge-forming layer 4 may have a shape which does not allow the recognition of its position.

According to this embodiment, the member 2 is formed from the core wire 3, and the bulge-forming layer 4 and the coating layer 5 are formed directly on the outer surface of the core wire 3. However, the guide wire disclosed here is not limited to this structure. For example, the core wire 3 may have on its outer surface one or more layers and may further have the bulge-forming layer 4 and the coating layer 5 on such layers. In this case, the member 2 has one or more layers on the outer surface of the core wire 3 such that they cover the outer surface partly or entirely.

Figure 3:
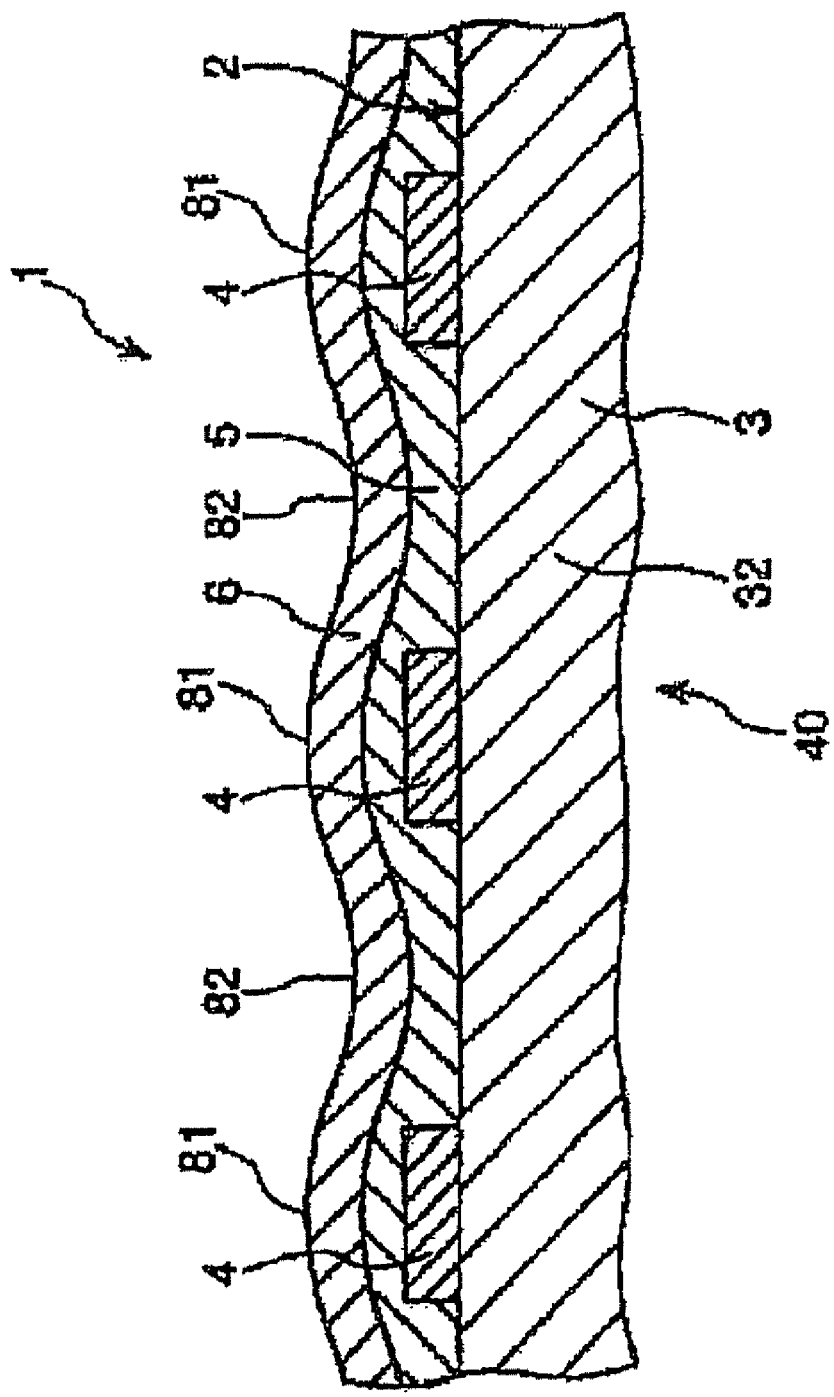
FIG. 3 is a partial longitudinal cross-sectional view of a part of a guide wire near the outer surface of the guide wire according to a second embodiment.
Figure 4:
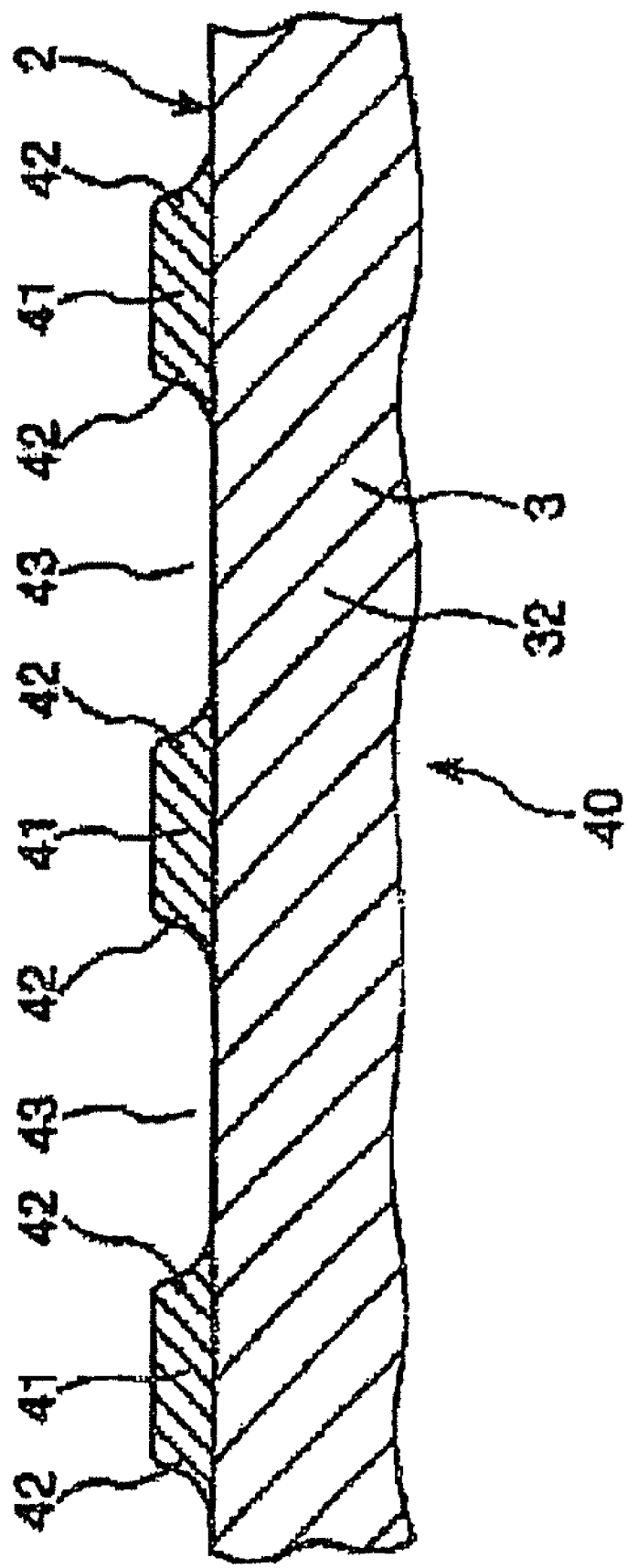
FIG. 4 is a partial longitudinal cross-sectional view of a part of the guide wire near the outer surface of the guide wire, illustrating a method for producing the guide wire shown in FIG. 3.

FIG. 3 illustrates a part of the guide wire near the outer surface of the guide wire in a second embodiment, while FIG. 4 shows a part near the outer surface of the guide wire. FIG. 4 is intended to illustrate a method for producing the guide wire shown in FIG. 3.

The guide wire 1 according to the second embodiment is described below. The description primarily describes differences between this embodiment and the first embodiment. Features in this embodiment that are common to the first embodiment are identified with the same reference numerals and a detailed description of such features is not repeated.

As shown in FIG. 3, the guide wire 1 according to the second embodiment has an outer layer 6 which covers the coating layer 5. This outer layer 6 possesses a transparency allowing the bulge-forming layer 4 to be visible. The outer layer 6 may cover the coating layer 5 partly or entirely (throughout the entire length). The outer surface of the outer layer 6 (or the outer surface of the guide wire 1) has the part where the bulge-forming layer 4 is formed and the part where the bulge-forming layer 4 is not formed, the former bulging relative to the latter, so that the bulging part 81 and the recessed part 82 are formed.

The outer layer 6 may be formed for various purposes. One purpose is to reduce the friction (sliding resistance) or improve the slidability of the guide wire 1, which contributes to the operability of the guide wire 1.

For the guide wire 1 to have reduced friction (sliding resistance), the outer layer 6 should be formed from a material which contains a resin (or a second resin) that reduces friction as mentioned below. As a result, the guide wire 1 decreases in friction (sliding resistance) with the lumen of the catheter (which is used in combination with the guide wire 1) and also with the lumen of the endoscope, which leads to improved operability. The reduced sliding resistance helps inhibit or preferably prevent the guide wire 1 from kinking when the guide wire 1 is moved or rotated in the lumen of the catheter or in the lumen of the endoscope.

The thickness of the outer layer 6 is not specifically restricted; it is usually about 1 to 15 µm, preferably about 2 to 10 µm. An excessively large thickness might physically affect the guide wire 1 and it is disadvantageous for the guide wire 1 to have a too-small diameter.

The bulge-forming layer 4 of the guide wire 1 is formed from a material containing a first resin and a pigment. And, the coating layer 5 is formed from a material containing a resin miscible with the first resin and a second resin differing from the miscible resin. Preferably, it should be formed from a material containing the first resin and a second resin differing from the first resin. Also, the outer layer 6 is formed from a material containing a resin miscible with the second resin, preferably a material containing the second resin.

Thus, the coating layer 5 functions as an adhesive layer (or adhesive) to bond the bulge-forming layer 4 and the outer layer 6 together. Therefore, even though the second resin contained in the outer layer 6 is one which hardly adheres to other members, the outer layer 6 protects itself from peeling. In other words, since the coating layer 5 and the bulge-forming layer 4 are formed from materials containing mutually miscible resins (or the first resin which is common to them), the bulge-forming layer 4 and the coating layer 5 firmly adhere (bond) to each other. In addition, since the outer layer 6 and the coating layer 5 are formed from the second resin which is common to them, the coating layer 5 and the outer layer 6 firmly adhere to each other. Thus, the coating layer 5 and the outer layer 6 protect themselves from peeling even when the guide wire 1 experiences bending and twisting repeatedly.

The bulge-forming layer 4 as a whole may contain the first resin in an amount about 1 to 90 wt %, preferably about 5 to 50 wt %, so that good adhesion is achieved between the bulge-forming layer 4 and the coating layer 5.

The coating layer 5 as a whole may contain a resin (e.g., the first resin) which is miscible with the first resin in the coating layer 5 in an amount of about 1 to 50 wt %, preferably about 3 to 35 wt %, so that good adhesion is achieved between the bulge-forming layer 4 and the coating layer 5.

The coating layer 5 as a whole may contain the second resin in an amount more than 50 wt %, preferably about 50 to 99 wt %, more preferably about 65 to 97 wt %, so that good adhesion is achieved between the coating layer 5 and the outer layer 6.

The outer layer 6 as a whole may contain the second resin in an amount of about 1 to 30 wt %, preferably about 3 to 20 wt %, or the outer layer 6 may be formed from a resin miscible with the second resin; for example the outer layer 6 can be made entirely of the second resin material, so that good adhesion is achieved between the coating layer 5 and the outer layer 6 and the guide wire 1 has reduced friction (or sliding resistance).

The first resin preferably is any one of resins (1) and (2) listed below.

(1) Heat-Resistant Resins Which Have a Melting Point of 200° C. or Higher, Preferably About 200 to 300° C.

Examples of the heat-resistant resins include polysulfone, polyimide, polyether-ether ketone, polyarylene ketone, polyphenylenesulfide, polyarylenesulfide, polyamideimide, polyetherimide, polyimidesulfone, polyarylsulfone, polyarylethersulfone, polyester, and polyethersulfone.

(2) Thermosetting Resins.

Examples of the thermosetting resins include epoxy resin, phenolic resin, unsaturated polyester resin, polyimide resin, silicone resin, and polyurethane resin. They may be used alone or in combination with one another.

The second resin to make the guide wire 1 decrease in friction (or sliding resistance) includes fluororesins, such as polytetrafluoroethylene (PTFE), ethylene-tetrafluoroethylene copolymer (ETFE), and tetrafluoroethylene-perfluoroalkylvinyl ether copolymer (PFA).

The following is a description of the method for producing the guide wire 1. This method, used to fabricate the second embodiment of the guide wire shown in FIGS. 3 and 4, can also be used to fabricate the first embodiment of the guide wire, except for the step pertaining to the formation of the outer layer 6.

(1) The first step is to prepare a liquid material for the bulge-forming layer 4 (composed of the constituent of the bulge-forming layer 4 and a solvent), a liquid material for the coating layer 5 (composed of the constituent of the coating layer 5 and a solvent), and a liquid material for the outer layer 6 (composed of the constituent of the outer layer 6 and a solvent).

Next, the liquid material for the bulge-forming layer 4 is applied to the bulge-forming region 40 on the outer surface of the core wire 3 (or the member 2), so that a coating film is formed entirely on the bulge-forming region 40. The coating film is dried.

Incidentally, the bulge-forming layer 4, the coating layer 5, and the outer layer 6 should have the appropriate thickness and other dimensions such as mentioned above by way of example.

(2) The coating film formed from the liquid material for the bulge-forming layer 4 is partly removed so that the bulge-forming layer 4 has a desired pattern.

The coating film should preferably be removed in such a way as to form fine surface irregularities in that part of the outer surface of the core wire 3 from which the coating film is removed (or the surface directly under the coating layer 5 at the part where the bulge-forming layer 4 is not formed in the bulge-forming region 40).

In this way it is possible to improve adhesion between the core wire 3 and the coating layer 5, and to prevent peeling of the coating layer 5. No additional steps are necessary because fine surface irregularities are formed at the same time as the coating film is removed.

No specific restrictions are imposed on the method of removing the liquid material for the bulge-forming layer. Typical methods include grinding (with a grinder) and laser ablation (with a laser radiator). These methods give rise to the fine surface irregularities simultaneously with the removal of the coating film.

When applied to the coating film 41 of the liquid material for the bulge-forming layer, grinding makes round the edge 42 of the coating film 41. The round edge 42 help prevent bubbles from remaining in the part 43 where the coating film 41 has been removed, when the liquid material for the coating film is applied (mentioned later), and the part 43 is completely filled with the liquid material for the coating film. Thus the coating film 5 is relatively reliably protected from peeling.

(3) The coating film of the liquid material for the bulge-forming layer and the outer surface of the core wire 3 are coated (over the entire length of the core wire 3) with the liquid material for the coating layer 5 so that a coating film thereof is formed. Thus the film of the liquid material for the coating layer 5 covers the coating film of the liquid material for the bulge-forming layer and the outer surface of the core wire 3 over the entire length of the core wire 3. Then, the coating film of the liquid material for the coating layer 5 is dried.

(4) The outer surface of the coating film of the liquid material for the coating layer is coated with the liquid material for the outer layer 6 over the entire length of the core wire 3, so that a coating film thereof is formed. Thus the film of the liquid material for the outer layer 6 covers the coating film of the liquid material for the coating layer over the entire length of the core wire 3. Then, the coating film of the liquid material for the outer layer 6 is dried. This step (4) is not included in the first embodiment mentioned above.

(5) The coating films formed (laminated) on the core wire 3 are baked, so that the bulge-forming layer 4, the coating layer 5, and the outer layer 6 are formed.

Adequate conditions should be established according to the composition of the materials constituting the bulge-forming layer 4, the coating layer 5, and the outer layer 6. The baking temperature should preferably be about 330 to 600° C., more preferably about 380 to 500° C., and the baking duration should preferably be about 1 to 60 minutes, more preferably about 3 to 30 minutes.

After baking, the outer layer 6 (or the coating layer 5 in the first embodiment) is finished with hydrophilic or hydrophobic lubricating coating, if necessary. Thus there is obtained the guide wire 1 as desired.

Figure 6:
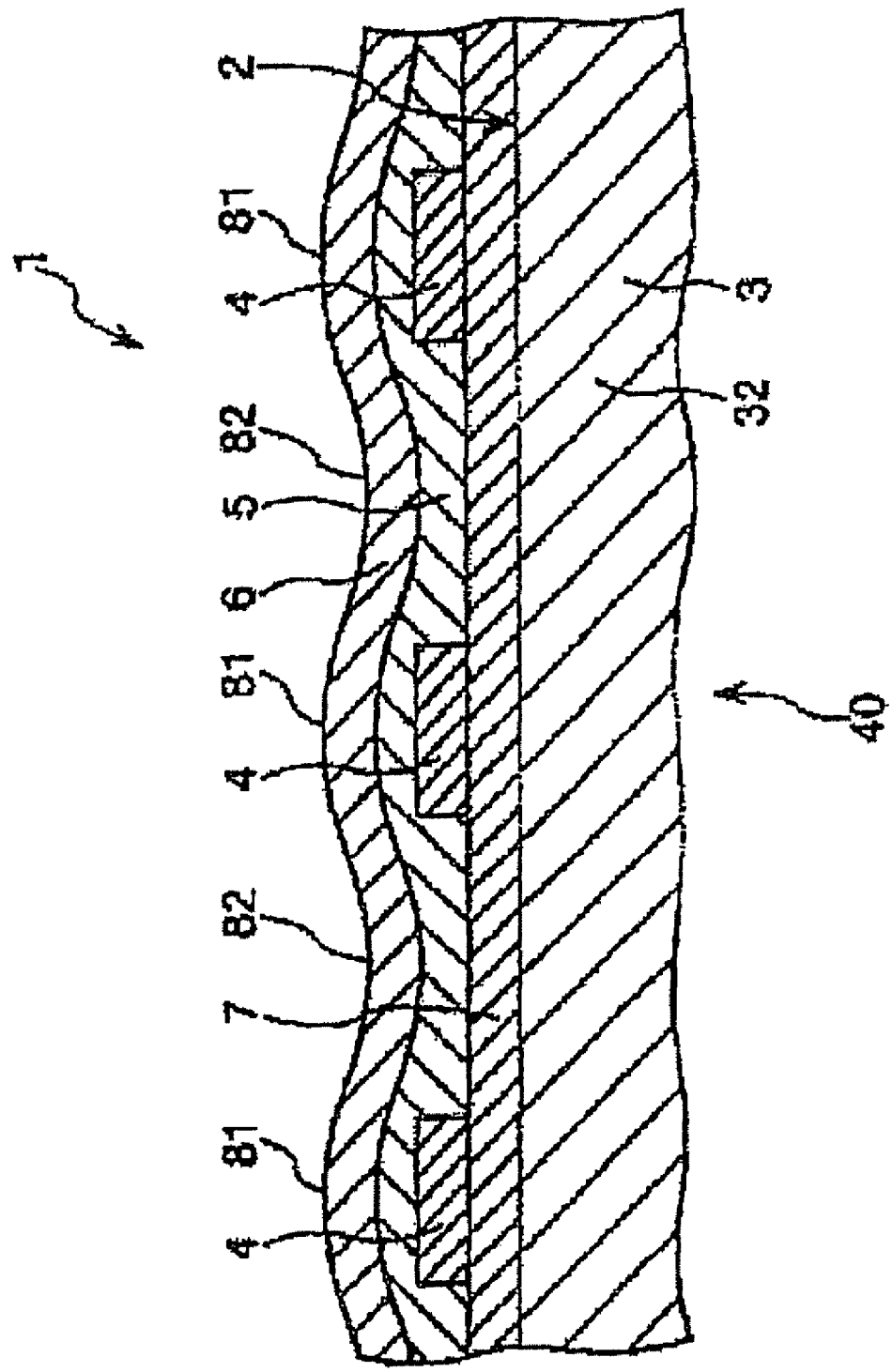
FIG. 6 is a partial longitudinal cross-sectional view of the part near the outer surface of the guide wire according to a fourth embodiment.
Figure 9:
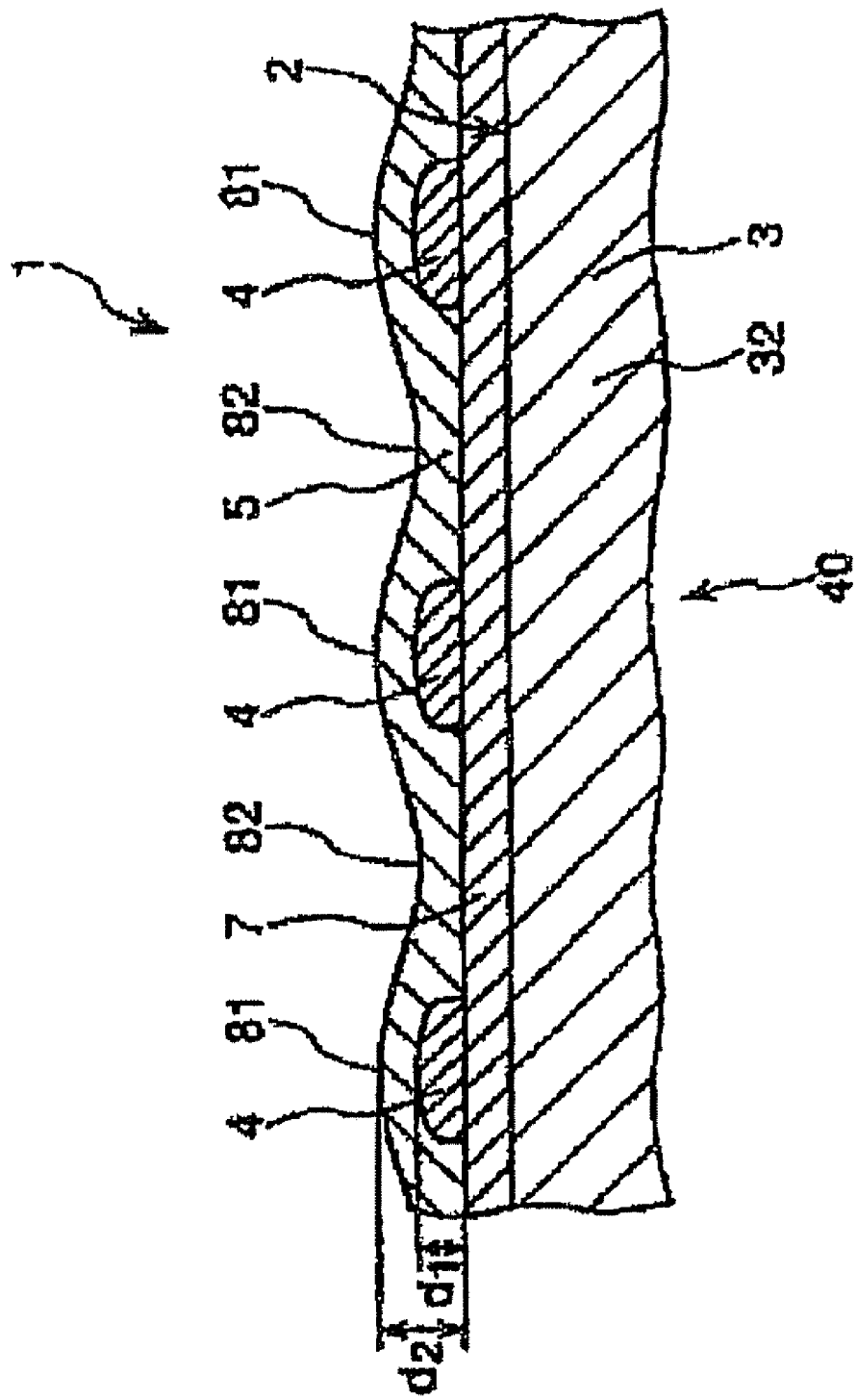
FIG. 9 is a partial longitudinal cross-sectional view of the part near the outer surface of the guide wire shown in FIG. 8.

Instead of above (1) and (2), the liquid material for the bulge-forming layer 4 can be applied to the bulge-forming region 40 on the outer surface of the core wire 3 or an undercoating layer 7 as shown in FIG. 6 or 9 so that the bulge-forming layer 4 has a desired pattern.

The guide wire 1 thus obtained produces the same effect as the guide wire 1 obtained in the first embodiment.

Incidentally, if the bulge-forming layer 4 is not required to function as a visible marker, the outer layer 6 may be opaque.

Figure 5:
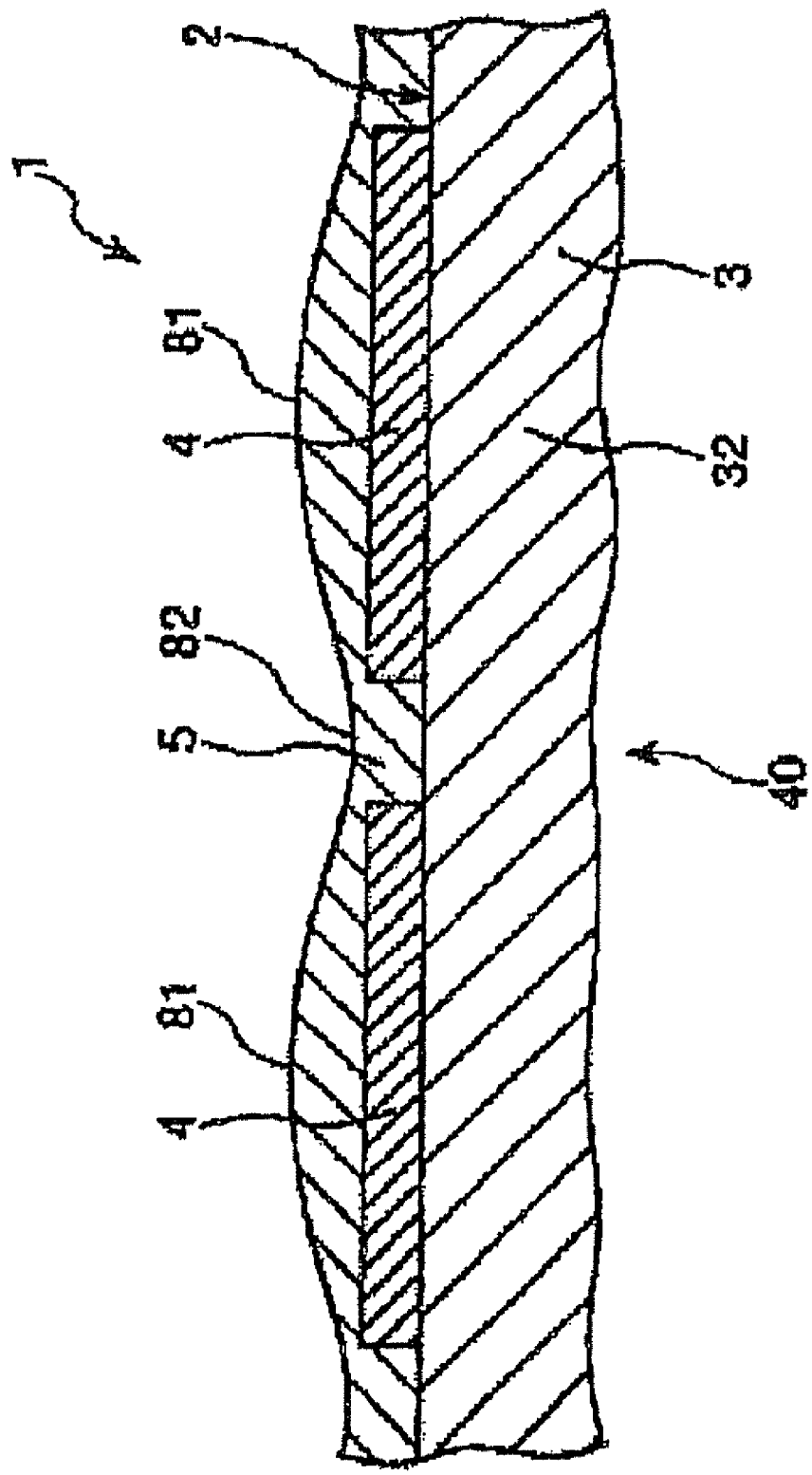
FIG. 5 is a partial longitudinal cross-sectional view of a part of the guide wire near the outer surface of the guide wire according to a third embodiment.

FIG. 5 is an illustration of the part of the guide wire near the outer surface of the guide wire according to a third embodiment.

The guide wire 1 according to the third embodiment is described below. The description primarily describes differences between this embodiment and the first embodiment. Features in this embodiment that are common to the first embodiment are identified with the same reference numerals and a detailed description of such features is not repeated.

In the guide wire 1 (shown in FIG. 5) according to the third embodiment, the coating layer 5 functions to reduce friction (sliding resistance) of the guide wire 1. The reduced friction contributes to the slidability and operability of the guide wire 1.

For the guide wire 1 to have reduced friction (sliding resistance), the coating layer 5 should be formed from a material which contains a resin (or a second resin) that reduces friction as mentioned below As a result, the guide wire 1 exhibits a decrease in friction (sliding resistance) with the lumen of the catheter (which is used in combination with the guide wire 1) and also with the lumen of the endoscope, which leads to improved operability. The reduced sliding resistance helps prevent the guide wire 1 from kinking when the guide wire 1 is moved or rotated in the lumen of the catheter or in the lumen of the endoscope.

The bulge-forming layer 4 of the guide wire 1 is formed from a material containing a first resin, a second resin differing from the first resin and a pigment. And, the coating layer 5 is formed from a material containing the second resin. In other words, both the constituent material of the coating layer 5 and the constituent material of the bulge-forming layer 4 contain a common second resin. Thus, the bulge-forming layer 4 and the coating layer 5 firmly adhere (bond) to each other, and the coating layer 5 is protected from peeling when the guide wire 1 experiences bending and twisting repeatedly, even though the coating layer 5 contains the second resin which hardly adheres to the other member.

The bulge-forming layer 4 as a whole may contain the second resin in an amount of about 1 to 30 wt %, preferably about 3 to 20 wt %, so that good adhesion is achieved between the bulge-forming layer 4 and the coating layer 5.

The coating layer 5 as a whole may contain the second resin in an amount of about 1 to 30 wt %, preferably about 3 to 20 wt %, or the coating layer 5 may be formed solely from the second resin, so that good adhesion is achieved between the bulge-forming layer 4 and the coating layer 5, and the guide wire 1 has reduced friction (or sliding resistance).

The first resin is preferably any one of resins (1) and (2) listed below.

(1) Heat-Resistant Resins Which Have a Melting Point of 200° C. or Higher, Preferably About 200 to 300° C.

Examples of the heat-resistant resins include polysulfone, polyimide, polyether-ether ketone, polyarylene ketone, polyphenylenesulfide, polyarylenesulfide, polyamideimide, polyetherimide, polyimidesulfone, polyarylsulfone, polyarylethersulfone, polyester, and polyethersulfone.

(2) Thermosetting Resins.

Examples of the thermosetting resins include epoxy resin, phenolic resin, unsaturated polyester resin, polyimide resin, silicone resin, and polyurethane resin. They may be used alone or in combination with one another.

The second resin includes fluororesins, such as polytetrafluoroethylene (PTFE), ethylene-tetrafluoroethylene copolymer (ETFE), and tetrafluoroethylene-perfluoroalkylvinyl ether copolymer (PFA). In the bulge-forming region 40, the area of the outer surface of the bulge-forming layer 4 is larger than that of the outer surface (immediately under the coating layer 5) of the core wire 3 where the bulge-forming layer 4 is not formed.

This structure results in a large area of contact between the bulge-forming layer 4 and the coating layer 5. Thus good adhesion is achieved between the bulge-forming layer 4 and the coating film 5. In this way the coating film 5 is reliably protected against peeling.

If S1 denotes the area of the outer surface of the bulge-forming layer 4 in the bulge-forming region 40 and S2 denotes the area of the outer surface (immediately under the coating layer 5) of the core wire 3 where the bulge-forming layer 4 is not formed in the bulge-forming region 40, the ratio of S1/S2 should preferably be about 1.5 to 10, more preferably about 3 to 8.

If the ratio of S1/S2 is larger than the upper limit given above (with the other conditions varied), there will be the possibility of the bulge-forming layer 4 decreasing in visibility. Also, if the ratio of S1/S2 is smaller than the lower limit given above, there will be the possibility of adhesion decreasing between the bulge-forming layer 4 and the coating layer 5.

The guide wire 1 thus obtained produces the same effect as the guide wire 1 obtained in the first embodiment mentioned above.

FIG. 6 illustrates the part near the outer surface of a guide wire according to a fourth embodiment.

The guide wire 1 according to the fourth embodiment is described below. The description primarily describes differences between this embodiment and the second embodiment. Features in this embodiment that are common to the second embodiment are identified with the same reference numerals and a detailed description of such features is not repeated.

As shown in FIG. 6, the guide wire 1 according to the fourth embodiment has the undercoating layer 7 which differs in color from the bulge-forming layer 4, and the bulge-forming layer 4 is formed partly on the outer surface of the undercoating layer 7.

The undercoating layer 7 covers the outer surface of the core wire 3 (or the member 2) at least in the bulge-forming region 40. According to this embodiment, the undercoating layer 7 covers the outer surface of the core wire 3 only in the bulge-forming region 40. This is not limitative; the undercoating layer 7 may cover the core wire 3 over its entire length.

The coating layer 5 firmly adheres to the undercoating layer 7 in that part of the bulge-forming region 40 at which the bulge-forming layer 4 is not formed.

The bulge-forming layer 4 of the guide wire 1 is formed from a material containing a first resin and a pigment, and the undercoating layer 7 is formed from a material containing a resin miscible with the first resin and a pigment different in color from the pigment in the bulge-forming layer 4. It should preferably be formed from a material containing the first resin and a pigment differing in color from the pigment of the bulge-forming layer 4. The color of the undercoating layer 7 depends mainly on the type and properties of the pigment contained therein, the type and properties (particularly color tone) of the resin contained therein, and the amount of the pigment contained therein. Any color can be obtained by adjustment of these factors.

Since the constituent material of the undercoating layer 7 and the constituent material of the bulge-forming layer 4 contain mutually miscible resins (particularly the first resin in common), the undercoating layer 7 and the bulge-forming layer 4 firmly adhere to each other. Therefore, the bulge-forming layer 4 protects itself from peeling even when the guide wire 1 experiences bending and twisting repeatedly.

The undercoating layer 7 as a whole may contain the resin (e.g., the first resin) miscible with the first resin in an amount of about 1 to 90 wt %, preferably about 5 to 50 wt %, so that good adhesion is achieved between the undercoating layer 7 and the bulge-forming layer 4.

The undercoating layer 7 as a whole may contain the pigment in an amount of about 10 to 99 wt %, preferably about 50 to 95 wt %, for a desired color, depending on the kind and properties of the pigment and the composition and characteristics of the resin material.

The pigment in the undercoating layer 7 may be uniformly dispersed. However, it may exist locally in the outer surface of the undercoating layer 7.

One or more than one kind of pigment may be used alone or in combination with one another (in the form of mixture). The one or more than one kind of pigment applies to both the undercoating layer 7 and the bulge-forming layer 4 having different colors relative to each other. The thickness of the undercoating layer 7 is not specifically restricted; it is usually about 1 to 20 μm, preferably about 2 to 10 μm.

The guide wire 1 thus obtained produces the same effect as the guide wire 1 obtained in the second embodiment mentioned above.

The advantage of the guide wire 1 is that the bulge-forming layer 4 and the undercoating layer 7 take on any desired color in response to the kind, properties, and amount of the pigment contained therein or the composition of the resin material contained therein. This offers a wide selection of colors for the visible marker and the undercoating layer 7, thereby giving a combination of the highly visible bulge-forming layer 4 and the undercoating layer 7. Thus the resulting guide wire 1 has a highly visible marker.

The fourth embodiment is also applicable to the first and third embodiments described above.

Figure 7:
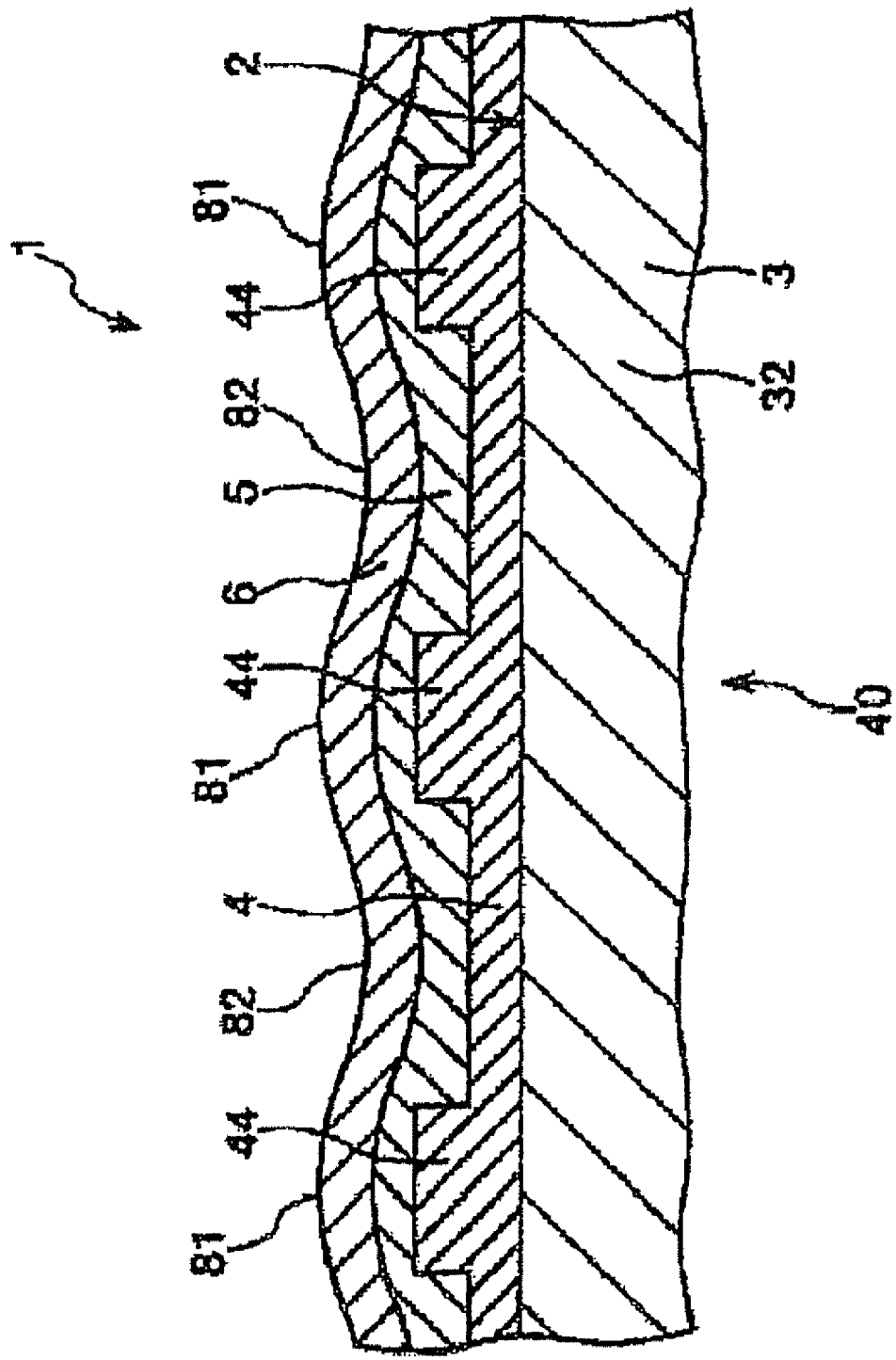
FIG. 7 is a partial longitudinal cross-sectional view of the part of the guide wire near the outer surface of the guide wire according to a fifth embodiment.

FIG. 7 illustrates a guide wire according to a further embodiment. More specifically, FIG. 7 shows the part near the outer surface of the guide wire according to a fifth embodiment.

The guide wire 1 according to the fifth embodiment is described below, primarily with reference to differences between this embodiment and the second embodiment. Features in this embodiment that are common to the second embodiment are identified with the same reference numerals and a detailed description of such features is not repeated.

In the guide wire 1 according to the fifth embodiment shown in FIG. 7, the bulge-forming layer 4 does not function as a visible marker, but rather functions as a means for the outer surface of the guide wire 1 to bulge (i.e., a means for forming the bulging part 81 and the recessed part 82).

The guide wire 1 has the bulge-forming layer 4 which is formed on the outer surface of the core wire 3 (or the member 2) in the bulge-forming region 40 so that the outer surface partly projects. In other words, the bulge-forming layer 4 has the partly projecting part 44 on the outer surface thereof.

The projecting part 44 is that part which corresponds to the bulge-forming layer 4 in the second embodiment mentioned above. On the outer surface of the outer layer 6 (or the outer surface of the guide wire 1), the part at which the projecting part 44 is formed (or the part corresponding to the projecting part of the bulge-forming layer 4) bulges relative to the part at which the projecting part 44 is not formed (or the part corresponding to the non-projecting part of the bulge-forming layer 4), so that the bulging part 81 and the recessed part 82 are formed.

The guide wire 1 thus obtained produces the same effect (except for the effect of visible marker) as the guide wire 1 obtained in the second embodiment mentioned above.

The fifth embodiment of the guide wire is also applicable to the first and third embodiments.

Figure 8:
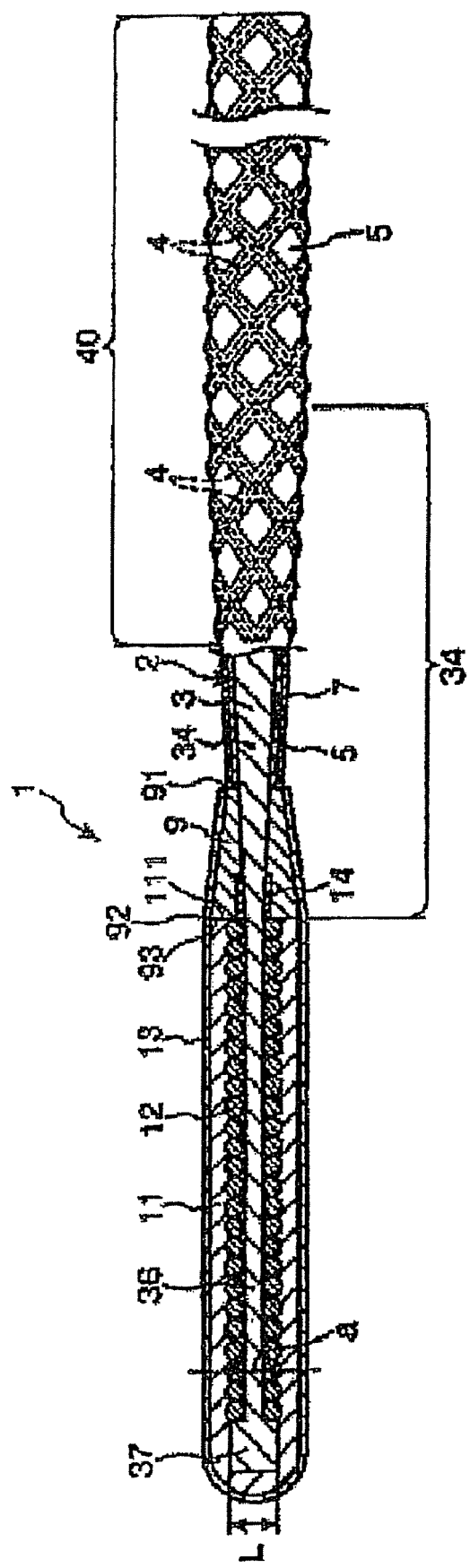
FIG. 8 is a partial longitudinal cross-sectional view of a sixth embodiment of the guide wire.

FIG. 8 shows a further embodiment of a guide wire. More specifically, FIG. 8 illustrates a sixth embodiment of the guide wire in longitudinal cross-sectional view, while FIG. 9 illustrates the part of the guide wire near the outer surface of the guide wire shown in FIG. 8. For the sake of convenience in description, the right and left sides in FIG. 8 are designated as the "base end" and the "forward end," respectively. In addition, to help facilitate an understanding, FIG. 8 schematically shows the guide wire with its length shortened and its thickness exaggerated. Therefore, the illustration is different from actual in the ratio of its thickness to length.

The guide wire 1 according to the fifth embodiment is described below, primarily with reference to differences between this embodiment and the first embodiment. Features in this embodiment that are common to the first embodiment are identified with the same reference numerals and a detailed description of such features is not repeated.

As shown in FIGS. 8 and 9, the guide wire 1 includes the member 2 (or the core wire 3), the spiral coil 12, the resin coating layer 11, the circular member 9 (step-filling member), the undercoating layer 7, the bulge-forming layer 4, the coating layer 5, and the hydrophilic lubricating layer 13.

The coil 12 is arranged around the forward end of the core wire 3 (or the member 2), i.e., around the small-diameter part 36 of the core wire 3. The coil 12 is a member which is formed by winding a thin wire around the small-diameter part 36 of the core wire 3 (or the member 2). In the case of the illustrated structure, the coil 12 is formed such that the adjacent wires are in contact with each other. In other words, the coil 12 is formed by tightly winding a thin wire around the core wire 3. In their natural state (without external force), the adjacent windings push against each other in the lengthwise direction of the member 2. Such compressive force in the natural state is not necessarily essential.

The coil 12 is wound such that it comes into contact with the outer surface of the small-diameter part 36 of the core wire 3. In other words, the inner surface of the coil 12 is in contact with the outer surface of the small-diameter part 36 of the core wire 3.

It is also possible for the coil 12 to be slipped on the small-diameter part 36 of the core wire 3, without contact between them. In other words, the thin wire of the coil 12 (inner surface of the coil 12) may be spaced away from the outer surface of the core wire 3. Also, the coil 12 may be wound such that the adjacent windings of the wire are not in contact with each other in the natural state without external force.

The coil 12 should preferably be formed from a metallic material, such as stainless steel, superelastic alloy, cobalt alloy, and noble metal (e.g., gold, platinum, and tungsten) and alloy thereof (e.g., platinum-iridium alloy). Noble metal opaque to X-rays is desirable because it permits the forward end of the guide wire 1 to be located when the guide wire 1 is inserted into a living body with the help of radioscopy. The coil 12 may be formed from different materials for its forward end and base end. For example, the forward end may be formed from a material opaque to X-rays and the base end may be formed from a material (such as stainless steel) relatively permeable to X-rays. The coil 12 may have an overall length of about 5 to 500 mm, which is not specifically restricted.

In this embodiment, the coil 12 is formed from a thin wire with a round cross section. However, the thin wire may have any cross section, such as ellipse, square, and rectangular.

The forward end of the core wire 3 is flat in shape (i.e., flat in cross-sectional shape). In other words, the core wire 3 has at its small-diameter part 36 the flat part 37 which is flat in shape. In the case of the illustrated structure, the flat part 37 is an approximately rectangular flat plate.

The width L of the flat part 37 (measured in the radial direction of the coil 12) is larger than the inside diameter a of the coil 12 (or the outside diameter D2 of the small-diameter part 36). And, the flat part 37 is located axially beyond, in the distal direction, the forward end of the coil 12. In other words, the coil 12 is arranged between the flat part 37 and the circular member 9 (mentioned later). The forward end of the coil 12 is engaged with a shoulder at the flat part 37, and the base end of the coil 12 is engaged with the forward end face 93 of the circular member 9.

This structure helps prevent the coil 12 from slipping off from the forward end of the core wire 3 (the member 2). Moreover, this structure reduces, and preferably eliminates, the need for material to fix the coil 12 to the core wire 3. Nevertheless, the coil 12 may be fixed to the core wire 3 by soldering or brazing or with an adhesive (boding agent), as a matter of course. The coil 12 may also be fixed by welding.

The flat part 37 may be formed by pressing. Specifically, pressing may be performed on the forward part of the core wire 3, with the small-diameter part 36 of the core wire 3 extended as much as the flat part 37. In this way the flat part 37 is formed at the forward end of the small-diameter part 36.

The guide wire 1 has the forward end of the core wire 3 (or the member 2), which includes the small-diameter part 36 and the flat part 37, and the resin coating layer 11 that covers the outer layer of the coil 12. The resin coating layer 11 firmly adheres to the flat part 37 of the core wire 3 and the outer surface of the coil 12.

The resin coating layer 11 is formed for various purposes, one of which it to ensure safe insertion of the guide wire 1 into a living body. For this reason, the resin coating layer 11 should preferably be formed from a flexible material (or soft and elastic material). In addition, it is desirable that the resin coating layer 11 be formed from a material which is more flexible than that for the bulge-forming layer 4, the coating layer 5, and the undercoating layer 7 (mentioned later).

Examples of the flexible material include polyolefins (such as polyethylene and polypropylene), polyvinyl chloride, polyester (such as PET and PBT), polyamide, polyimide, polyurethane, polystyrene, silicone resin, thermoplastic elastomers (such as polyurethane elastomer, polyester elastomer, and polyamide elastomer), rubbers (such as latex gum and silicone rubber), and composite materials thereof.

The resin coating film 11 formed from any one of the foregoing thermoplastic elastomers or rubbery materials makes the forward end of the guide wire 1 more flexible. Hence it contributes to safety without the possibility of damaging the internal wall when the guide wire 1 is inserted into a living body.

The resin coating film 11 should preferably contain fine particles (filler) dispersed therein which are opaque to X-rays (functioning as a contrast medium), so that it permits the forward end of the guide wire 1 to be located at the time of insertion into a living body with the help of radioscopy. The foregoing particles may be formed any material opaque to X-rays, such as gold, platinum, tungsten, and alloy thereof (such as platinum-iridium alloy).

The thickness of the resin coating film 11 is not specifically restricted; it depends on the object, material, and fabricating method. A preferred thickness is about 20 to 500 µm, more preferably about 30 to 300 µm. With an excessively small thickness, the resin coating film 11 may not fully produce its effect. With an excessively large thickness, the resin coating film 11 may adversely affect the physical properties of the member 2 (or the guide wire 1). The resin coating layer 11 may be a laminate composed of two or more layers.

The base end of the resin coating layer 11 is a certain distance away from the forward end of the coating layer 5 and the undercoating layer 7 (mentioned later). There is the circular member 9 which fills the gap of the step between the base end of the resin coating layer 11 and the member 2. The circular member 9 tightly encloses the outer surface of the tapered part 34 of the core wire 3. The forward end 92 of the circular member 9 is at the base end of the resin coating layer 11 and the base end 91 of the circular member 9 is at the forward end of the undercoating layer 7 and the coating layer 5.

The outside diameter of the base end of the resin coating layer 11 is larger than that of the member 2 at the base end of the resin coating layer 11, and the above-mentioned gap between the steps is due to the difference in the outside diameters.

The outside diameter of the forward end 92 of the circular member 9 is approximately equal to that of the base end of the resin coating layer 11, so that the forward end 93 of the circular member 9 closely adheres to the base end face 111 of the resin coating layer 11. In this case, the resin coating layer 11 does not extend toward the base end beyond the forward end 92 of the circular member 9 and does not overlap the circular member 9. In other words, there is a stepless continuous surface between the forward end 92 of the circular member 9 and the base end of the resin coating layer 11.

The outside diameter of the circular member 9 gradually decreases in going from the forward end toward the base end, so that the outside diameter of the base end 91 of the circular member 9 is smaller than the outside diameter of the forward end 92. And, the outside diameter of the base end 91 of the circular member 9 is approximately equal to the outside diameter of the coating layer 5 at the base end 91 of the circular member 9. In other words, there is a stepless continuous surface between the coating layer 5 and the base end 91 of the circular member 9. The outside diameter 91 of the circular member 9 is smaller than the outside diameter of the main body 32 of the core wire 3. The base end 91 of the circular member 9 is positioned closer to the forward end than the base end 341 of the tapered part (See FIG. 1). The circular member 9 is 0.5 to 15 mm long.

The inside diameter of the base end 91 of the circular member 9 is larger than the inside diameter of the forward end 92. This is because the circular member 9 is positioned at the tapered part 34 of the core wire 3. It is also possible that the inside diameter of the base end 91 is identical with that of the forward end 92.

The circular member 9 prevents the base end of the resin coating layer 11 from being caught by the forward end of the catheter (to be used in combination with the guide wire 1) or by the medical instrument such as the stand of the endoscope. In this way it is possible to prevent the resin coating layer 11 from peeling and also to prevent the guide wire 1 from decreasing in slidability due to the step mentioned above.

The hardness of the circular member 9 should be higher than that of the resin coating layer 11. In this way it is possible to prevent the circular member 9 from being caught by the forward end of the catheter (to be used in combination with the guide wire 1) or by the medical instrument such as the stand of the endoscope.

The circular member 9 may have its forward end face 93 and/or the inner surface roughened. Surface irregularities on the forward end face 93 contribute to adhesion to the resin coating layer 11, and surface irregularities on the inner surface contribute to adhesion to the core wire 3 and the fixing material 14 (mentioned later).

The circular member 9 may be formed from any material, such as resins and metals, without specific restrictions. The constituent material may be identical with or different from that for the resin coating layer 11.

However, the circular member 9 should preferably be formed from a metallic material or a hard resin material, with the former being particularly desirable.

The hard resin material for the circular member 9 includes polycarbonate, polyamide (nylon), polyethylene terephthalate, polyacetal, and polyphenylene sulfide.

The metallic material for the circular member 9 includes stainless steel, titanium, titanium alloy, Ni—Ti alloy, aluminum, gold, and platinum. Noble metals (such as gold and platinum) and alloys thereof are preferable because they function as a good contrast medium for X-rays.

In the case where the circular member 9 is formed from a metallic material, its outer surface may be covered with a coating layer (no shown). This coating layer may be formed from any material such as resins, ceramics, and metals, which are not specifically restricted. Insulating materials are particularly desirable.

The circular member 9 is fixed to the core wire 3 (or the member 2) by the fixing material 14 arranged on the outer surface of the tapered part 34 of the core wire 3.

The fixing material 14 may be solder or adhesive. An insulating adhesive is particularly desirable.

The method for fixing the circular member 9 is not limited to one employing the fixing material.

In the illustrated structure, the whole body of the circular member 9 is positioned at the tapered part 34. However, an instance is permissible in which only a portion of the circular member 9 is positioned at the tapered part 34.

The circular member 9 functions to relieve difference in stiffness (flexural and torsional stiffness) between the base end side and forward end side (beyond the circular member 9) of the member 2. The circular member 9 prevents stiffness from abruptly increasing at the base end of the resin coating layer 11, thereby helping to avoid kinking at the base end of the resin coating layer 11.

The guide wire 1 should preferably have at least the outer surface of its forward end coated with the hydrophilic lubricating layer 13 formed from a hydrophilic material. In this embodiment, the hydrophilic lubricating layer 13 covers the outer surface of the guide wire 1 (or the outer surface from the base end 91 to the forward end of the circular member 9 of the guide wire 1) in the region from the forward end of the guide wire 1 to the base end 91 of the circular member 9 (the forward end of the undercoating layer 7 and the coating layer 5), or the outer surface of the resin layer 11 and the circular member 9. The hydrophilic material produces lubricity upon getting wet, thereby reducing the friction (sliding resistance) and improving the slidability of the guide wire 1. This contributes to the operability of the guide wire 1.

The hydrophilic material includes cellulosic high-molecular materials, polyethylene oxide high-molecular materials, maleic anhydride high-molecular materials (such as methyl vinyl ether-maleic anhydride copolymer), acrylamide high-molecular materials (such as polyacrylamide, polyglycidyl methacrylate-dimethyl acrylamide (PGMA-DMAA) block copolymer), water-soluble nylon, polyvinyl alcohol, and polyvinyl pyrrolidone.

These hydrophilic compounds usually exhibit lubricity upon moisture (water) absorption, thereby reducing frictional resistance (sliding resistance) due to contact with the lumen of the catheter (to be used in combination with the guide wire 1) and the lumen of the endoscope. Such lubricity improves the slidability and operability of the guide wire 1 in the lumen of the catheter and the lumen of the endoscope.

The guide wire 1 has the undercoating layer 7 which differs in color from the bulge-forming layer 4. The bulge-forming layer 4 is formed partly on the outer surface of the undercoating layer 7. As shown in FIG. 8, the bulge-forming layer 4 is formed in a grid-like pattern. And, the bulge-forming region 40 extends from the base end of the core wire 3 to the midway of the tapered part 34 (the position closer to the base end side than the circular member 9). However, it may extend over the entire length of the core wire 3.

The undercoating layer 7 covers the outer surface of the core wire 3 (or the member 2) in at least the bulge-forming region 40. In this embodiment, the undercoating layer 7 extends from the base end of the core wire 3 to the base end 91 of the circular member 9. And, the coating layer 5 adheres to the undercoating layer 7 at the part where the bulge-forming layer 4 is not formed in the bulge-forming region 40.

Incidentally, the undercoating layer 7 may also cover the outer surface of the core wire 3 only in the bulge-forming region 40 or may entirely cover the core wire 3 (along the overall length).

The undercoating layer 7 is formed from a material containing a resin and a pigment differing in color from the pigment for the bulge-forming layer 4. The color of the undercoating layer 7 depends mainly on the type and properties of the pigment contained therein, the type and properties (particularly color tone) of the resin contained therein, and the amount of the pigment contained therein. Any color can be obtained by adjustment of these factors.

The constituent material of the undercoating layer 7 may contain at least one of the resins which is preferably miscible with the resin contained in the constituent material of the bulge-forming layer 4, and it is desirable to use common resins. In other words, it is desirable that the constituent material of the undercoating layer 7 and the constituent material of the bulge-forming layer 4 contain mutually miscible resins, preferably common resins. This results in firm adhesion between the bulge-forming layer 4 and the undercoating layer 7. Thus, the bulge-forming layer 4 protects itself from peeling even when the guide wire 1 experiences bending and twisting repeatedly.

The undercoating layer 7 as a whole may contain the miscible resin (particularly common resins) mentioned above in an amount of about 1 to 90 wt %, preferably about 5 to 50 wt %, so that good adhesion is achieved between the undercoating layer 7 and the bulge-forming layer 4.

The undercoating layer 7 and the coating layer 5 should preferably be formed from materials containing mutually miscible resin, desirably common resins, so that good adhesion is achieved between the coating layer 5 and the undercoating layer 7 in the region where the bulge-forming layer 4 is not formed. Thus the coating layer 5 protects itself from peeling even when the guide wire 1 experiences bending and twisting repeatedly. The content of pigment in the undercoating layer 7 as a whole depends on the type and properties of the pigment and the composition and characteristics of the resin; it is usually about 10 to 99 wt %, preferably about 50 to 95 wt %.

The pigment in the undercoating layer 7 should be uniformly dispersed. However, it may exist locally in the outer surface of the undercoating layer 7.

One or more than one kind of pigment may be used alone or in combination with one another (in the form of mixture). The one or more than one kind of pigment applies to both the undercoating layer 7 and the bulge-forming layer 4 having different relative colors.

The thickness of the undercoating layer 7 is not specifically restricted; it is usually about 1 to 20 μm, preferably about 2 to 10 μm, and more preferably about 3 to 8 μm.

The thickness d1 (maximum thickness) of the bulge-forming layer 4 is also not specifically restricted; it is usually about 1 to 30 μm, preferably about 2 to 10 μm, more preferably 3 to 8 μm.

The total thickness of the coating layer 5 and the bulge-forming layer 4 is not specifically restricted. The total value d2 (maximum value) of the coating film 5 and the bulge-forming layer 4 in the bulging part 81 may be 50 μm or smaller. It should preferably be about 2 to 40 μm, more preferably about 4 to 30 μm, and most desirably about 15 to 25 μm.

The guide wire 1 according to this embodiment produces the same effect as the guide wire 1 according to the first embodiment mentioned above.

The advantage of the guide wire 1 is that the bulge-forming layer 4 and the undercoating layer 7 take on any desired color in response to the kind, properties, and amount of the pigment contained therein or the composition of the resin material contained therein. This offers a wide selection of colors for the visible marker and the undercoating layer 7, thereby giving a combination of the highly visible bulge-forming layer 4 and the undercoating layer 7 regardless of the color of the core wire 3 (the member 2). Thus the resulting guide wire 1 has a highly visible marker.

The sixth embodiment is also applicable to the second and third embodiments mentioned above.

Figure 10:
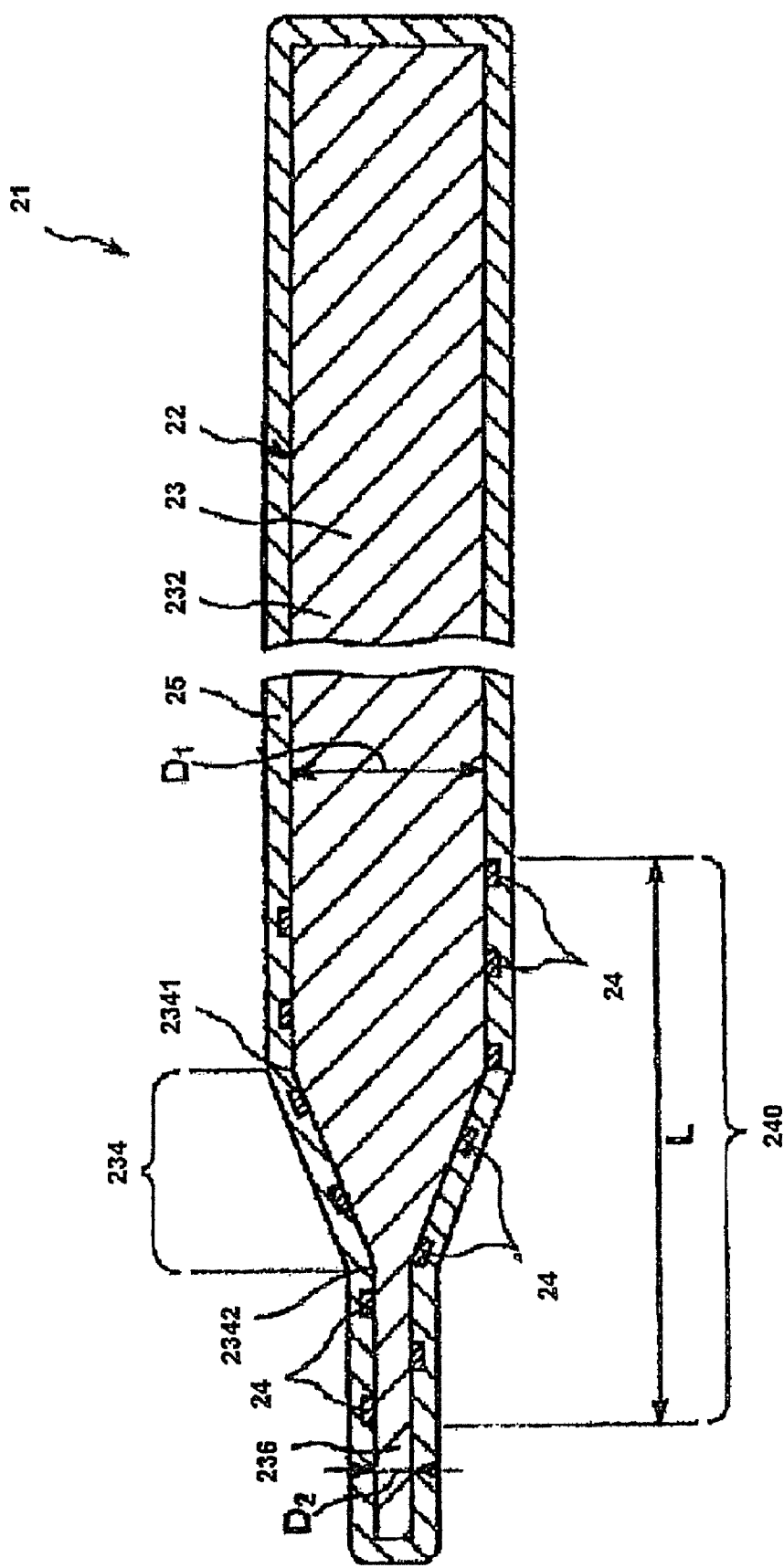
FIG. 10 is a longitudinal cross-sectional view of a seventh embodiment of the guide wire.

FIG. 10 is a longitudinal cross-sectional view of a seventh embodiment of the guide wire. As shown in FIG. 10, the guide wire 21 includes a member 22, a marker-forming layer 24, and a coating layer 25. The member 22 is a flexible core wire 23. The marker-forming layer 24 differs in color from the member 22 (or the core wire 23). The coating layer 25 has such transparency (light transmission) as to make the marker-forming layer 24 visible.

According to this embodiment, the member 22 is a single continuous core wire 23 and has a round cross section. However, the member 22 may be composed of two or more different or identical core wires joined together by welding or brazing. It may also have any additional structure.

The guide wire 21 is not specifically restricted in its overall length. A preferred overall length is about 200 to 5,000 mm. Also, it is not specifically restricted in outside diameter. A preferred outside diameter is about 0.2 to 1.2 mm.

The core wire 23 extends over the entire length of the guide wire 21. It includes a main part 232 (which corresponds to the main body of the guide wire 21), a tapered part 234 (which is close to the forward end), and a thin part 236 (at the forward end). The main part 232 has a constant outside diameter (inclusive of nearly constant). The tapered part 234 gradually decreases in outside diameter toward the forward end. The thin part 236 also has a constant outside diameter (inclusive of nearly constant).

The tapered part 234 makes the core wire 23 gradually (continuously) increase in flexibility from the boundary (or the base end 2341 of the tapered part) between the main part 232 and the tapered part 234 toward the forward end. This adds flexibility to the guide wire 21, thereby making it easier and safer to insert the guide wire 21 into a living body.

The thin part 236 that extends in an elongated manner toward the forward end from the tapered part 234 is more flexible than the rest of the guide wire. The main part 232 of the core wire 23 has an outside diameter D1 (measured at the base end 2341 of the tapered part), which is not specifically restricted but should preferably be about 0.3 to 1.0 mm, more preferably about 0.4 to 0.7 mm.

The thin part 236 of the core wire 23 has an outside diameter D2 (measured at the forward end 2342 of the tapered part), which is not specifically restricted but should preferably be about 0.05 to 0.3 mm, more preferably about 0.1 to 0.2 mm. The outside diameter of the thin part 236 may be constant or may gradually decrease in going toward the forward end.

The length of the tapered part 234 may vary depending on the use and kind of the guide wire without specific restrictions. It should preferably be about 10 to 300 mm, more preferably about 30 to 250 mm.

The length of the thin part 236 is not specifically restricted. It should preferably be about 0 to 100 mm, more preferably about 10 to 50 mm.

The tapered part 234 may decrease in outside diameter at a constant rate or a varying rate along the lengthwise direction of the core wire 23 (the member 22). There may be two or more of the tapered part 234.

The core wire 23 should preferably have minute surface irregularities. This is true particularly for that part of the outer surface (immediately under the coating layer 25) where the marker-forming layer 24 in the marker-forming region 240 (mentioned later) is not yet formed. The surface irregularities improve adhesion between the core wire 23 and the coating layer 25, thereby preventing the coating layer 25 from peeling off.

The core wire 23 may be made of metallic materials, such as stainless steel, Ni—Ti alloy, Ni—Al alloy, Cu—Zn alloy, and other superelastic alloys, or resin materials having a comparatively high stiffness. They may be used alone or in combination with one another.

The guide wire 21 according to the present invention is not specifically restricted in its application. It may be used, for example, to guide a catheter to a desired position (such as a cavity in a living body) through the lumen of an endoscope. (It will be referred to as "transendoscopic guide wire.") The embodiment mentioned below is concerned typically with the case in which the guide wire 21 is used as a transendoscopic guide wire.

The transendoscopic guide wire has a visible marker on its outer surface, so that the marker is visible through the endoscope. In this embodiment, the marker-forming layer 24 functions as the visible marker.

The guide wire 21 has the marker-forming region 240 in which the marker-forming layer 24 is formed. On the outer layer of the core wire 23 (or the member 22) in the marker-forming region 240 is a portion of the marker-forming layer 24. In other words, the marker-forming layer 24 is formed tightly on the outer surface of the core wire 23 at prescribed intervals, and the coating layer 25 between individual marker-forming layers 24 is formed tightly on the core wire 23. The marker-forming layer 24 differs in color from the outer surface of the core wire 23 (or the member 22), so that it functions as the visible marker.

The marker-forming region 240 may extend entirely or partly (along the overall length) in the lengthwise direction of the core wire 23. In this embodiment, the marker-forming region 240 is formed in the forward section of the core wire 23 including the tapered part 234.

The marker-forming region 240 may have a length L in the lengthwise direction which is not specifically restricted. The length L should preferably be about 10 to 50 cm, more preferably about 20 to 40 cm.

The marker-forming layer 24 may be formed from a material containing a resin and a pigment. The color of the marker-forming layer 24 depends mainly on the kind, amount, and properties of the pigment contained therein and also on the composition and properties (especially color) of the resin material contained therein. Any color can be produced by their adequate combination.

The color of the marker-forming layer 24 is important for the operator to observe the movement of the guide wire 21 through the endoscope. An adequate color should be selected in view of the color of the core wire 23 (or the member 22) underneath.

To cite an example, the core wire 23 or its oxide coating film may have a silver white color (metallic color) or a grayish or black color, and the marker-forming layer 24 may have a reddish or yellowish color. In this case there is a large difference in brightness between them, which gives rise to a high contract. Thus the marker-forming layer 24 is highly visible, which is desirable. Another case in which they have complementary colors is also desirable because of the high visibility of the marker-forming layer 24. A high contrast is obtained when a dark color such as black (or dark colors such as charcoal gray, dark brown, navy blue, and violet) is combined with a light color (such as yellow, yellowish green, and orange), or when blue is combined with red, orange, or pink. A high contrast is also obtained by combination of the same colors differing in shade, such as dark blue with light blue and reddish-brown with pink.

The constituent material of the marker-forming layer 24 may contain any resin without specific restrictions. However, any one of resins (1) and (2) listed below is preferable.

(1) Heat-Resistant Resins Which Have a Melting Point of 200° C. or Higher, Preferably About 200 to 300° C.

Examples of the heat-resistant resins include polysulfone, polyimide, polyether-ether ketone, polyarylene ketone, polyphenylenesulfide, polyarylenesulfide, polyamideimide, polyetherimide, polyimidesulfone, polyarylsulfone, polyarylethersulfone, polyester, polyethersulfone, and fluororesin, such as polytetrafluoroethylene (PTFE) and ethylene-tetrafluoroethylene copolymer (ETFE). They may be used alone or in combination with one another.

(2) Thermosetting Resins.

Examples of the thermosetting resins include epoxy resin, phenolic resin, unsaturated polyester resin, polyimide resin, silicone resin, and polyurethane resin. They may be used alone or in combination with one another.

The marker-forming layer 24 as a whole should contain pigment in an amount of about 10 to 99 wt %, preferably about 50 to 95 wt %, to produce desired colors. An adequate amount depends on the type and properties of the pigment and the composition and properties of the resin material. The marker-forming layer 24 should preferably contain pigment uniformly distributed therein, although uneven distribution in its outer surface is permissible.

Pigments may be used alone or in combination with one another in the form of mixture.

The marker-forming layer 24 is not specifically restricted in shape (pattern) and dimensions. However, it should preferably have a thickness of about 1 to 20 μm, more preferably about 2 to 10 μm, so that the guide wire 21 can be made thin.

As shown in the figure, the marker-forming layer 24 takes on a spiral pattern. The spiral (or circular) pattern has a width of about 1 to 10 mm and extends over about 10 to 50 cm in the lengthwise direction of the guide wire 21, at intervals of about 1 to 10 mm.

The shape of the marker-forming layer 24 is not restricted to spiral or circular. It can also be in the form of a straight line, wavy pattern, polka dots, check pattern, and mesh pattern. The shape of the marker-forming layer 24 can also include numerals, letters, symbols, and graduations, which are visible. Two or more different patterns may be combined with each other (for example, a spiral pattern and a circular pattern placed on top of the other) for better visibility.

The pigment may be either inorganic pigments or organic pigments, with the former being preferable because of their good heat resistance. Inorganic pigments include carbon black, mica, titanium dioxide, nickel-titanium yellow, prussian blue, milori blue, cobalt blue, ultramarine, and viridian blue.

The coating layer 25 has such transparency as to make the marker-forming layer 24 visible. It covers the marker-forming layer 24 and the core wire 23 (or the member 22) in at least the marker-forming region 240. In this embodiment, the coating layer 25 covers not only the marker-forming region 240 but also the marker-forming layer 24 and the entire length of the core wire 23. The coating layer 25 is formed from a resin-containing material. As shown in FIG. 10, the coating layer 25 where the marker-forming layer 24 is located has a substantially constant outer diameter.

The constituent material of the coating layer 25 may contain any resin which is not specifically restricted. At least one of the resins should be the one which is miscible with the resin contained in the constituent material of the marker-forming layer 24. In other words, mutually miscible resins should be contained in the constituent material for the coating layer 25 and the constituent material for the marker-forming layer 24. This helps ensure relatively firm adhesion between the marker-forming layer 24 and the coating layer 25, thereby helping to prevent the coating layer 25 from peeling off even when the guide wire 21 experiences repeated bending and twisting.

"Miscibility" means that the two components dissolve well each other thermodynamically. In other words, they do not separate from each other after curing.

Mutually miscible resins may be the same ones or different ones. Combination of different resins is that of polyamideimide and polyimide, polyetherimide and polyimide, polyamideimide and polyetherimide, or polysulfone and polyethersulfone, which have common groups, such as imide and sulfone.

The content of the mutually miscible resins in the marker-forming layer 24 should preferably be about 1 to 90 wt %, more preferably about 5 to 50 wt %, based on the total weight of the marker-forming layer 24, for good adhesion between the marker-forming layer 24 and the coating layer 25.

The content of the mutually miscible resins in the coating layer 25 should preferably be about 1 to 50 wt %, more preferably about 3 to 35 wt %, based on the total weight of the coating layer 25, for good adhesion between the marker-forming layer 24 and the coating layer 25.

The coating layer 25 is not specifically restricted in thickness. It should preferably have a thickness of about 1 to 20 µm, more preferably about 2 to 10 µm.

The total thickness of the coating layer 25 and the marker-forming layer 24 is not specifically restricted; it should be equal to or smaller than 50 µm, preferably about 2 to 40 µm, more preferably about 4 to 20 µm.

The foregoing thickness is necessary for the guide wire 21 to have a small diameter. This object is not achieved with the conventional visible marker, which is formed by covering the core wire with a heat-shrinkable tube (as thick as about 100 µm) having a spiral or parallel stripy pattern. In this embodiment, the marker-forming layer 24 and the coating layer 25 having the foregoing thickness can be formed easily and certainly by using the structure (mentioned above) and the production method (mentioned later).

The method for producing the guide wire 21 is not specifically discussed here, but will be mentioned later together with the method for producing the guide wire 21 according to the eighth embodiment.

As mentioned above, the guide wire 21 according to the seventh embodiment has a small diameter, and the marker-forming layer 24 thereon has any desired color owing to adequate selection of pigment and resin material (for composition and amount). The marker-forming layer 24 allows a wide selection of colors for any color of the core wire 23 (or the member 22). Therefore, the resulting guide wire 21 has an easily visible marker.

Since the coating layer 25 and the marker-forming layer 24 are formed from mutually miscible resins, they firmly adhere to each other and the coating layer 25 remains without peeling off even when the guide wire 21 experiences bending and twisting repeatedly.

According to this embodiment, the member 22 is formed from the core wire 23, and the marker-forming layer 24 and the coating layer 25 are formed directly on the outer surface of the core wire 23. However, the guide wire is not limited to this structure. For example, the core wire 23 may have on its outer surface one or more layers and may further have the marker-forming layer 24 and the coating layer 25 on such layers. In this case, the member 22 has one or more layers on the outer surface of the core wire 23 such that they cover the outer surface partly or entirely.

Figure 11:
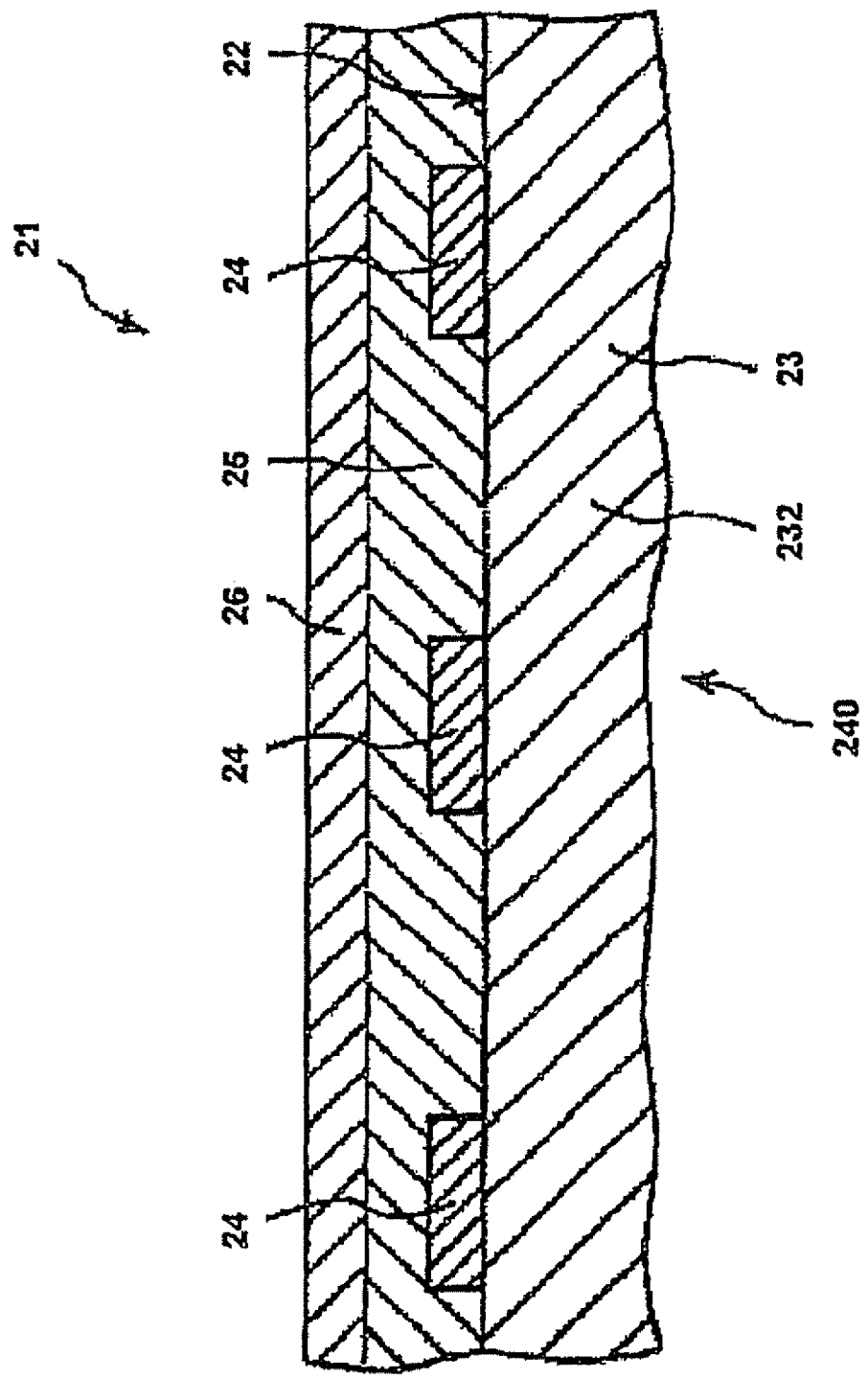
FIG. 11 is a partial longitudinal cross-sectional view of the marker-forming region in an eighth embodiment of the guide wire.
Figure 12:
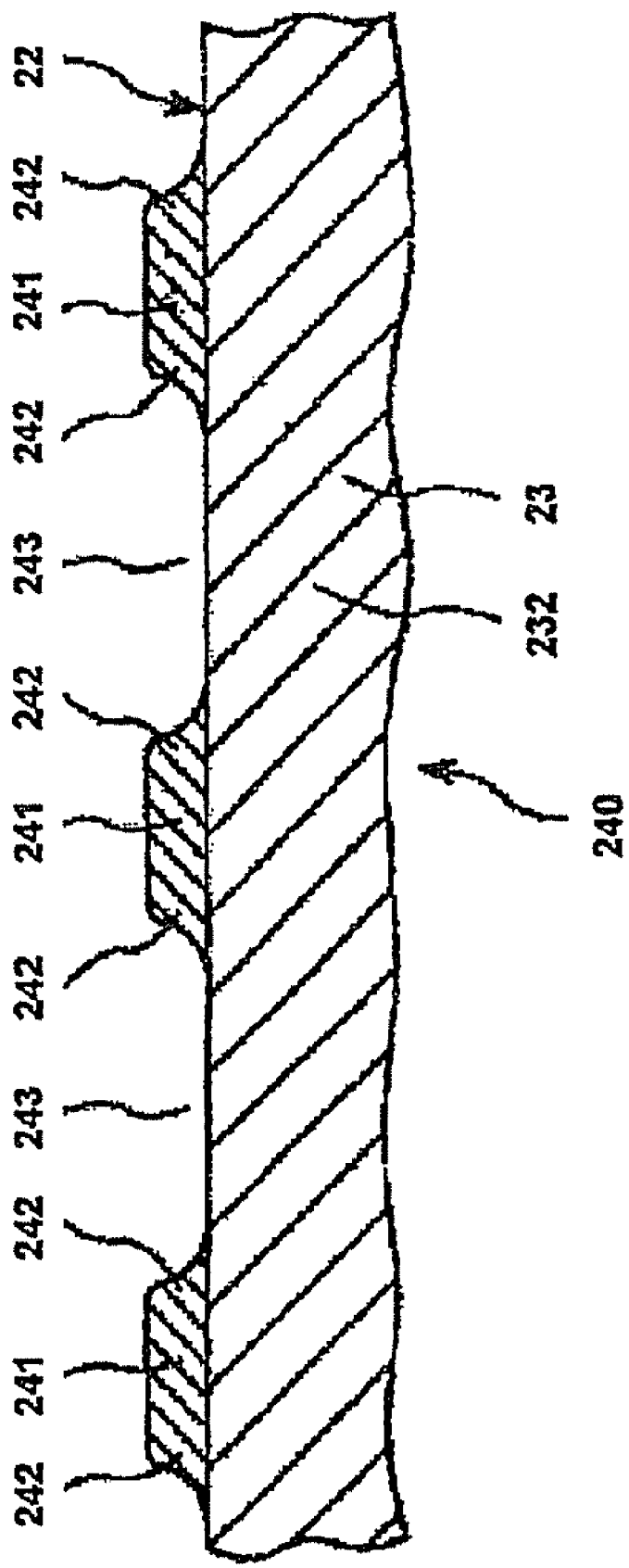
FIG. 12 is a partial longitudinal cross-sectional view of the marker-forming region, illustrating the method for producing the guide wire shown in FIG. 11.

FIG. 11 is a partial longitudinal cross-sectional view of the marker-forming region in an eighth embodiment of the guide wire. FIG. 12 shows the marker-forming region of the guide wire. FIG. 12 schematically illustrates an aspects of the method for producing the guide wire shown in FIG. 11.

The guide wire 21 according to the eighth embodiment is described below. The description primarily describes differences between this embodiment and the seventh embodiment. Features in this embodiment that are common to the seventh embodiment are identified with the same reference numerals and a detailed description of such features is not repeated.

As shown in FIG. 11, the guide wire 21 according to the eighth embodiment has an outer layer 26 which covers the coating layer 25 and has such transparency as to make the marker-forming layer 24 visible. The outer layer 26 may cover the coating layer 25 partly or entirely (throughout the entire length).

The outer layer 26 may be formed for various purposes. One purpose is to reduce the friction (sliding resistance) or improve the slidability of the guide wire 21, which contributes to the operability of the guide wire 21.

For the guide wire 21 to have reduced friction (sliding resistance), the outer layer 26 should be formed from a material which contains a resin (or a second resin) that reduces friction as mentioned below. As a result, the guide wire 21 exhibits a decrease in friction (sliding resistance) relative to the lumen of the catheter (which is used in combination with the guide wire 21) and also with respect to the lumen of the endoscope, which leads to improved operability. The reduced sliding resistance helps prevent the guide wire 21 from kinking when the guide wire 21 is moved or rotated in the lumen of the catheter or in the lumen of the endoscope.

As shown in FIG. 11, the outer layer 26 where the marker-forming layer 24 is located has a substantially constant outer diameter.

The thickness of the outer layer 26 is not specifically restricted; it is usually about 1 to 15 µm, preferably about 2 to 10 µm. An excessively large thickness might physically affect the guide wire 21 and is disadvantageous for the guide wire 21 to have a small diameter.

The marker-forming layer 24 of the guide wire 21 is formed from a material containing a first resin and a pigment. And, the coating layer 25 is formed from a material containing a resin miscible with the first resin and a second resin differing from the miscible resin. Preferably, it should be formed from a material containing the first resin and a second resin differing from the first resin. Also, the outer layer 26 is formed from a material containing the second resin.

Thus, the coating layer 25 functions as an adhesive layer (or adhesive) to bond the marker-forming layer 24 and the outer layer 26 together. Therefore, even though the second resin contained in the outer layer 26 is one which hardly adheres to other members, the outer layer 26 protects itself from peeling. In other words, since the coating layer 25 and the marker-forming layer 24 are formed from materials containing mutually miscible resins (or the first resin which is common to them), the marker-forming layer 24 and the coating layer 25 firmly adhere (bond) to each other, and, since the outer layer 26 and the coating layer 25 are formed from the second resin which is common to them, the coating layer 25 and the outer layer 26 firmly adhere to each other. Thus, the coating layer 25 and the outer layer 26 protect themselves from peeling even when the guide wire 21 experiences bending and twisting repeatedly.

The marker-forming layer 24 as a whole may contain the first resin in an amount of about 1 to 90 wt %, preferably about 5 to 50 wt %, so that good adhesion is achieved between the marker-forming layer 24 and the coating layer 25.

The coating layer 25 as a whole may contain a resin (e.g., the first resin) which is miscible with the first resin in the coating layer 25 in an amount of about 1 to 50 wt %, preferably about 3 to 35 wt %, so that good adhesion is achieved between the marker-forming layer 24 and the coating layer 25.

The coating layer 25 as a whole may contain the second resin in an amount equal to or more than 50 wt %, preferably about 50 to 99 wt %, more preferably about 65 to 97 wt %, so that good adhesion is achieved between the coating layer 25 and the outer layer 26.

The outer layer 26 as a whole may contain the second resin in an amount of about 1 to 30 wt %, preferably about 3 to 20 wt %, or the outer layer 26 should be formed solely from the second resin, so that good adhesion is achieved between the coating layer 25 and the outer layer 26 and the guide wire 21 has reduced friction (or sliding resistance).

The first resin is not specifically restricted. However, it should preferably be any one of resins (1) and (2) listed below.

(1) Heat-Resistant Resins Which Have a Melting point of 200° C. or Higher, Preferably About 200 to 300° C.

Examples of the heat-resistant resins include polysulfone, polyimide, polyether-ether ketone, polyarylene ketone, polyphenylenesulfide, polyarylenesulfide, polyamideimide, polyetherimide, polyimidesulfone, polyarylsulfone, polyarylethersulfone, polyester, and polyethersulfone.

(2) Thermosetting Resins.

Examples of the thermosetting resins include epoxy resin, phenolic resin, unsaturated polyester resin, polyimide resin, silicone resin, and polyurethane resin. They may be used alone or in combination with one another.

The second resin to make the guide wire 21 decrease in friction (or sliding resistance) includes fluororesins, such as polytetrafluoroethylene (PTFE), ethylene-tetrafluoroethylene copolymer (ETFE), and tetrafluoroethylene-perfluoroalkylvinyl ether copolymer (PFA).

The following is a description of the method for producing the guide wire 21 according to this eighth embodiment, it being understood that this method is also applicable to the fabrication of the seventh embodiment of the guide wire except for aspects of the method pertaining to the outer layer 26.

(1) The first step is to prepare a liquid material for the marker-forming layer 24 (composed of the constituent of the marker-forming layer 24 and a solvent), a liquid material for the coating layer 25 (composed of the constituent of the coating layer 25 and a solvent), and a liquid material for the outer layer 26 (composed of the constituent of the outer layer 26 and a solvent).

Next, the liquid material for the marker-forming layer 24 is applied to the marker-forming region 240 on the outer surface of the core wire 23 (or the member 22), so that a coating film is formed entirely on the marker-forming region 240. The coating film is dried.

Incidentally, the marker-forming layer 24, the coating layer 25, and the outer layer 26 should have the thickness and other dimensions as mentioned above, which are not repeated here.

(2) The coating film formed from the liquid material for the marker-forming layer 24 is partly removed so that the marker-forming layer 24 has a desired pattern.

The coating film should preferably be removed in such a way as to form fine surface irregularities in that part of the outer surface of the core wire 23 from which the coating film is removed (or the surface directly under the coating layer 25 at the part where the marker-forming layer 24 is not formed in the marker-forming region 240).

In this way it is possible to improve adhesion between the core wire 23 and the coating layer 25 and to prevent peeling of the coating layer 25. No additional steps are necessary because fine surface irregularities are formed at the same time as the coating film is removed.

In the case of a core wire made of Ni—Ti alloy, for example, the surface is covered with oxide film and the oxide film peels off as the coating film is removed, so that the silver white color of Ni—Ti alloy appears. This color produces a high contrast if an adequate color is used for the marker-forming layer 24.

No specific restrictions are imposed on the method of removing the liquid material for the marker-forming layer. Typical methods include grinding (with a grinder) and laser ablation (with a laser radiator). These methods give rise to the fine surface irregularities simultaneously with the removal of the coating film.

When applied to the coating film 241 of the liquid material for the marker-forming layer, grinding makes round the edge 242 of the coating film 241, as shown in FIG. 12. The round edge 242 prevents bubbles from remaining in the part 243 where the coating film 41 has been removed, when the liquid material for the coating film is applied (mentioned later), and the part 243 is completely filled with the liquid material for the coating film. Thus the coating film 25 is surely protected from peeling.

(3) The coating film of the liquid material for the marker-forming layer 24 and the outer surface of the core wire 23 are coated (over the entire length of the core wire 23) with the liquid material for the coating layer 25 so that a coating film thereof is formed. Thus the film of the liquid material for the coating layer 25 covers the coating film of the liquid material for the marker-forming layer and the outer surface of the core wire 23 over the entire length of the core wire 23. Then, the coating film of the liquid material for the coating layer is dried.

The coating film of the liquid material for the coating layer 25 is not necessarily required to cover the entire length of the core wire 23 so long as it covers the marker-forming region 240.

(4) The outer surface of the coating film of the liquid material for the coating layer is coated with the liquid material for the outer layer 26 over the entire length of the core wire 23, so that a coating film thereof is formed. Thus the film of the liquid material for the outer layer 26 covers the coating film of the liquid material for the coating layer over the entire length of the core wire 23. Then, the coating film of the liquid material for the outer layer is dried. This step (4) is not included in the seventh embodiment mentioned above.

(5) The coating films formed (laminated) on the core wire 23 are baked, so that the marker-forming layer 24, the coating layer 25, and the outer layer 26 are formed.

Adequate conditions should be established according to the composition of the materials constituting the marker-forming layer 24, the coating layer 25, and the outer layer 26. The baking temperature should preferably be about 330 to 600° C., more preferably about 380 to 500° C., and the baking duration should preferably be about 1 to 60 minutes, more preferably about 3 to 30 minutes.

After baking, the outer layer 26 is finished with hydrophilic or hydrophobic lubricating coating, if necessary. Thus there is obtained the guide wire 21 as desired.

The guide wire 21 thus obtained produces the same effect as the guide wire 21 obtained in the seventh embodiment.

Figure 13:
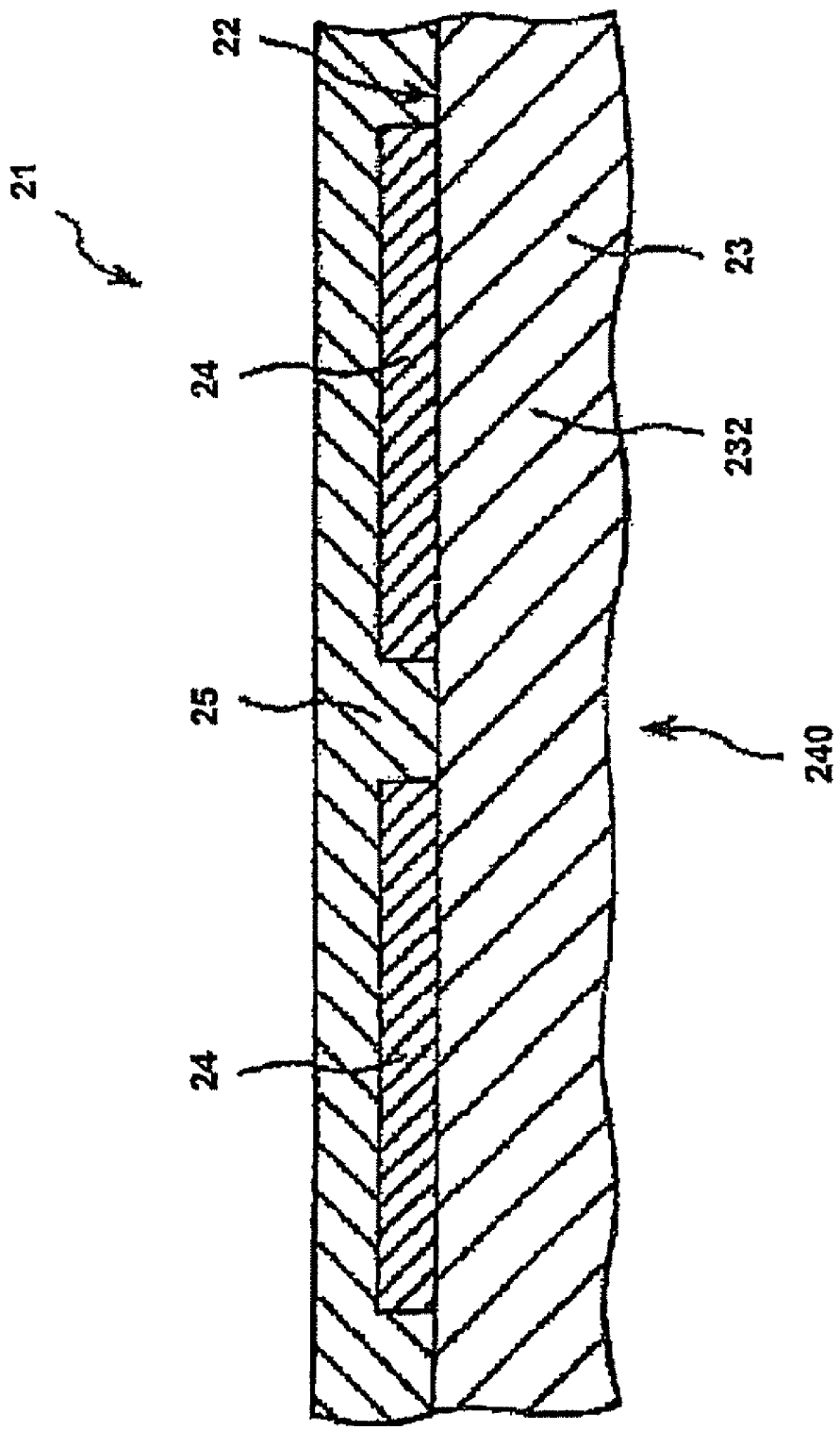
FIG. 13 is a partial longitudinal cross-sectional view of the marker-forming region in a ninth embodiment of the guide wire.

FIG. 13 illustrates the marker-forming region in a ninth embodiment of the guide wire.

The guide wire 21 according to the ninth embodiment is described below. The description primarily describes differences between this embodiment and the seventh embodiment. Features in this embodiment that are common to the seventh embodiment are identified with the same reference numerals and a detailed description of such features is not repeated.

In the ninth embodiment of the guide wire 21 shown in FIG. 13, the coating layer 25 functions to reduce friction (sliding resistance) of the guide wire 21. The reduced friction contributes to the slidability and operability of the guide wire 21.

For the guide wire 21 to have reduced friction (sliding resistance), the coating layer 25 should be formed from a material which contains a resin (or a second resin) that reduces friction as mentioned below. As a result, the guide wire 21 exhibits decreased friction (sliding resistance) with the lumen of the catheter (which is used in combination with the guide wire 21) and also with the lumen of the endoscope, which leads to improved operability. The reduced sliding resistance contributes to preventing the guide wire 21 from kinking when the guide wire 21 is moved or rotated in the lumen of the catheter or in the lumen of the endoscope.

The marker-forming layer 24 of the guide wire 21 is formed from a material containing a first resin, a second resin differing from the first resin, and a pigment. And, the coating layer 25 is formed from a material containing the second resin. In other words, both the constituent material of the coating layer 25 and the constituent material of the marker-forming layer 24 contain the common second resin. Thus, the marker-forming layer 24 and the coating layer 25 firmly adhere (bond) to each other, and the coating layer 25 protects itself from peeling when the guide wire 21 experiences bending and twisting repeatedly, even though the coating layer 25 contains the second resin which hardly adheres to the other member.

The marker-forming layer 24 as a whole may contain the second resin in an amount of about 1 to 30 wt %, preferably about 3 to 20 wt %, so that good adhesion is achieved between the marker-forming layer 24 and the coating layer 25.

The coating layer 25 as a whole may contain the second resin in an amount of about 1 to 30 wt %, preferably about 3 to 20 wt %, or the coating layer 25 may be formed solely from the second resin, so that good adhesion is achieved between the marker-forming layer 24 and the coating layer 25 and the guide wire 21 has reduced friction (or sliding resistance).

The first resin is not specifically restricted. However, it should preferably be any one of resins (1) and (2) listed below.

(1) Heat-Resistant Resins Which Have a Melting Point of 200° C. or Higher, Preferably about 200 to 300° C.

Examples of the heat-resistant resins include polysulfone, polyimide, polyether-ether ketone, polyarylene ketone, polyphenylenesulfide, polyarylenesulfide, polyamideimide, polyetherimide, polyimidesulfone, polyarylsulfone, polyarylethersulfone, polyester, and polyethersulfone.

(2) Thermosetting Resins.

Examples of the thermosetting resins include epoxy resin, phenolic resin, unsaturated polyester resin, polyimide resin, silicone resin, and polyurethane resin. They may be used alone or in combination with one another.

The second resin includes fluororesins, such as polytetrafluoroethylene (PTFE), ethylene-tetrafluoroethylene copolymer (ETFE), and tetrafluoroethylene-perfluoroalkylvinyl ether copolymer (PFA). In the marker-forming region 240, the area of the outer surface of the marker-forming layer 24 is larger than that of the outer surface (immediately under the coating layer 25) of the core wire 23 where the marker-forming layer 24 is not formed.

This structure results in a large area of contact between the marker-forming layer 24 and the coating layer 25. Thus good adhesion is achieved between the marker-forming layer 24 and the coating layer 25. In this way the coating layer 25 surely protects itself from peeling.

If S1 denotes the area of the outer surface of the marker-forming layer 24 in the marker-forming region 240 and S2 denotes the area of the outer surface (immediately under the coating layer 25) of the core wire 23 where the marker-forming layer 24 is not formed in the marker-forming region 240, then the ratio of S1/S2 should preferably be about 1.5 to 10, more preferably about 3 to 8.

If the ratio of S1/S2 is larger than the upper limit given above (with the other conditions varied), there will be the possibility of the marker-forming layer 24 decreasing in visibility. Also, if the ratio of S1/S2 is smaller than the lower limit given above, there will be the possibility of adhesion decreasing between the marker-forming layer 24 and the coating layer 25.

The guide wire 21 thus obtained produces the same effect as the guide wire 21 obtained in the seventh embodiment mentioned above.

Figure 14:
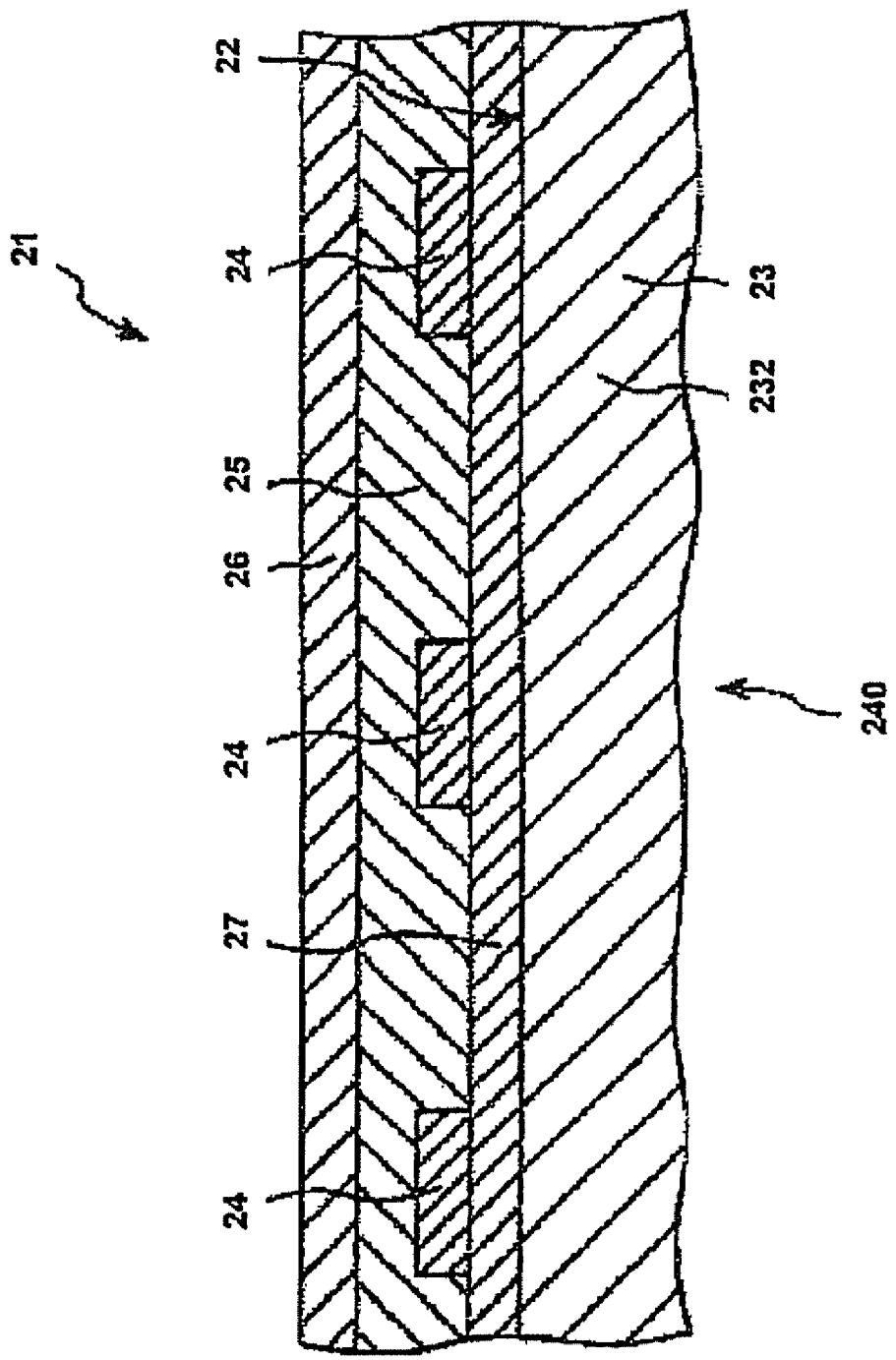
FIG. 14 is a partial longitudinal cross-sectional view of the marker-forming region in a tenth embodiment of the guide wire.

FIG. 14 is a longitudinal cross-sectional view of the marker-forming region in a tenth embodiment of the guide wire disclosed here.

The guide wire 21 according to the tenth embodiment is described below, primarily with reference to differences between this embodiment and the eight embodiment of the guide wire. Features in this embodiment that are common to the eighth embodiment are identified with the same reference numerals and a detailed description of such features is not repeated.

As shown in FIG. 14, the guide wire 21 according to the tenth embodiment includes the undercoating layer 27 which differs in color from the marker-forming layer 24, and the marker-forming layer 24 is formed partly on the outer surface of the undercoating layer 27.

The undercoating layer 27 covers the outer surface of the core wire 23 (or the member 22) at least in the marker-forming region 240. According to this embodiment, the undercoating layer 27 covers the outer surface of the core wire 23 only in the marker-forming region 240. This is not limitative as the undercoating layer 27 may cover the core wire 23 over its entire length.

The marker-forming layer 24 of the guide wire 21 is formed from a material containing a first resin and a pigment, and the undercoating layer 27 is formed from a material containing a resin miscible with the first resin and a pigment different in color from the pigment in the marker-forming layer 24. It should preferably be formed from a material containing the first resin and a pigment differing in color from the pigment of the marker-forming layer 24. The color of the undercoating layer 27 depends mainly on the type and properties of the pigment contained therein, the type and properties (particularly color tone) of the resin contained therein, and the amount of the pigment contained therein. Any color can be obtained by adjustment of these factors.

Since the constituent material of the undercoating layer 27 and the constituent material of the marker-forming layer 24 contain mutually miscible resins (particularly the first resin in common), the undercoating layer 27 and the marker-forming layer 24 firmly adhere to each other. Therefore, the marker-forming layer 24 protects itself from peeling even when the guide wire 21 experiences bending and twisting repeatedly.

The undercoating layer 27 as a whole may contain the resin (e.g., the first resin) miscible with the first resin in an amount of about 1 to 90 wt %, preferably about 5 to 50 wt %, so that good adhesion is achieved between the undercoating layer 27 and the marker-forming layer 24.

The undercoating layer 27 as a whole may contain the pigment in an amount of about 10 to 99 wt %, preferably about 50 to 95 wt %, for a desired color, depending on the kind and properties of the pigment and the composition and characteristics of the resin material.

The pigment in the undercoating layer 27 should be uniformly dispersed. However, it may exist locally in the outer surface of the undercoating layer 27.

One or more than one kind of pigment may be used alone or in combination with one another (in the form of mixture).

The thickness of the undercoating layer 27 is not specifically restricted; it is usually about 1 to 20 μm, preferably about 2 to 10 μm.

The guide wire 21 thus obtained produces the same effect as the guide wire 21 obtained in the eighth embodiment mentioned above.

The advantage of the guide wire 21 is that the marker-forming layer 24 and the undercoating layer 27 take on any desired color in response to the kind, properties, and amount of the pigment contained therein or the composition of the resin material contained therein. This offers a wide selection of colors for the visible marker and the undercoating layer 27, thereby giving a combination of the highly visible marker-forming layer 24 and the undercoating layer 27 regardless of the color of the core wire 23 (the member 22). Thus the resulting guide wire 21 has a highly visible marker.

The aspects of the tenth embodiment of the guide wire are also applicable to the seventh and ninth embodiments.

Figure 15:
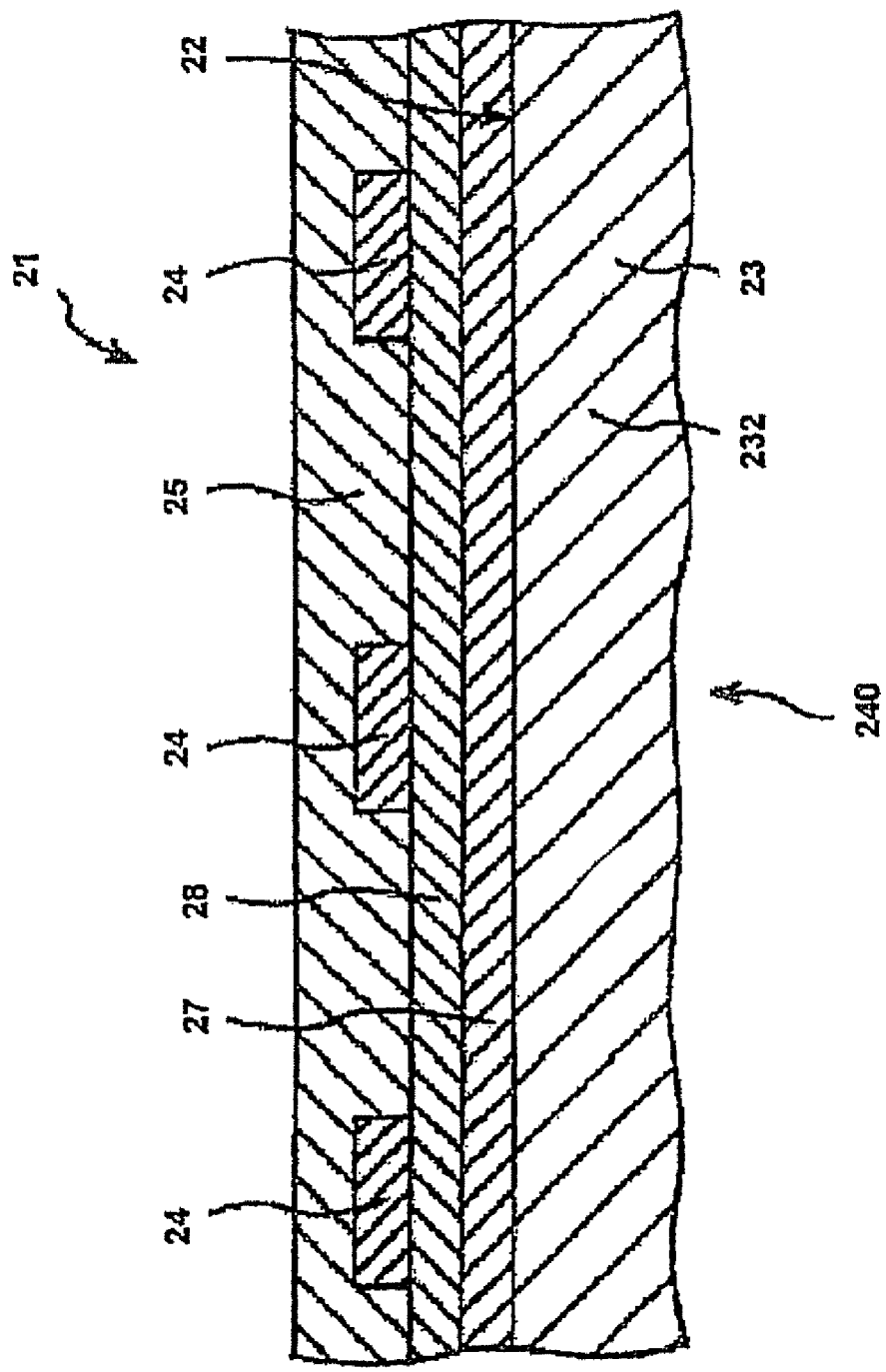
FIG. 15 is a partial longitudinal cross-sectional view of the marker-forming region in an eleventh embodiment of the guide wire.

FIG. 15 illustrates the marker-forming region according to an eleventh embodiment of the guide wire.

The guide wire 21 according to the eleventh embodiment is described below. The description primarily describes differences between this embodiment and the seventh embodiment. Features in this embodiment that are common to the seventh embodiment are identified with the same reference numerals and a detailed description of such features is not repeated.

As shown in FIG. 15, the guide wire 21 according to the eleventh embodiment has the undercoating layer 27 and an intermediate layer 28, and the marker-forming layer 24 is formed partly on the outer surface of the intermediate layer 28 (or above the intermediate layer 28).

The undercoating layer 27 covers the outer surface of the core wire 23 (or the guide member 22) at least in the marker-forming region 240. In this embodiment, the undercoating layer 27 covers the outer surface of the core wire 23 only in the marker-forming region 240. However, modifications are possible in which the undercoating layer 27 covers the core wire 23 entirely (over the entire length thereof), or has a color different from that of the marker-forming layer 24.

Also, the intermediate layer 28 covers the outer surface of the undercoating layer 27. In this embodiment, the intermediate layer 28 is formed only in the marker-forming region 240. However, modifications are possible in which the intermediate layer 28 covers the entire length of the core wire 23, or has a color different from that of the marker-forming layer 24.

The coating layer 25 that reduces friction (or sliding resistance) makes the guide wire 21 easy to operate.

For the guide wire 21 to have improved operability with reduced friction (or sliding resistance), it is desirable to make the coating layer 25 from a material containing a resin (mentioned below) which reduces friction. In this way, the guide wire 21 exhibits decreased friction (sliding resistance) with the lumen of the catheter (which is used in combination with the guide wire 21) and also with the lumen of the endoscope, which leads to improved operability. The reduced sliding resistance prevents the guide wire 21 from kinking when the guide wire 21 is moved or rotated in the lumen of the catheter or in the lumen of the endoscope.

The marker-forming layer 24 is formed from a material containing a resin and a pigment. The composition of the material is exemplified by Compositions (1) to (3) below.

(Composition 1)

A material contains a second resin (mentioned later, which differs from the first resin), and a pigment. The second resin should preferably be any of fluororesins mentioned in the eighth embodiment.

The marker-forming layer 24 as a whole should contain the second resin in an amount of about 1 to 90 wt %, preferably about 5 to 50 wt %, so that good adhesion is achieved between the marker-forming layer 24 and the coating layer 25 or between the marker-forming layer 24 and the intermediate layer 28.

(Composition 2)

A material contains a second resin (mentioned later, which differs from the first resin), a third resin (which differs from the second resin), and a pigment.

The second and third resins should be mutually different fluororesins used in the eighth embodiment. For example, a combination of PTFE and PFA is preferable. The first and third resins should also be mutually different.

The marker-forming layer 24 as a whole should contain the second resin in an amount of about 1 to 81 wt %, preferably about 5 to 45 wt %, so that good adhesion is achieved between the marker-forming layer 24 and the coating layer 25 or between the marker-forming layer 24 and the intermediate layer 28.

Also, the marker-forming layer 24 as a whole should contain the third resin in an amount of about 1 to 81 wt %, preferably about 5 to 45 wt %, so that good adhesion is achieved between the marker-forming layer 24 and the coating layer 25.

(Composition 3)

A material contains a second resin (mentioned later, which differs from the first resin), a fourth resin (which differs from the second resin), and a pigment.

The second resin should be a fluororesin used in the eighth embodiment. The fourth resin should be a heat-resistant resin used in the eighth embodiment, which has a melting point of 200° C. or higher, preferably about 200 to 300° C. The fourth resin should be a thermosetting resin used in the eighth embodiment. The second and fourth resins should be mutually different. For example, a combination of PFA and polyimide is preferable. The first and fourth resins may be mutually different or the same.

The marker-forming layer 24 as a whole may contain the second resin in an amount of about 1 to 30 wt %, preferably about 3 to 20 wt %, so that good adhesion is achieved between the marker-forming layer 24 and the coating layer 25 or between the marker-forming layer 24 and the intermediate layer 28.

The marker-forming layer 24 as a whole may contain the fourth resin in an amount of about 1 to 60 wt %, preferably about 3 to 30 wt %, so that good adhesion is achieved between the marker-forming layer 24 and the intermediate layer 28.

The coating layer 25 is formed from a material containing a resin (mentioned later) differing from the first resin. It should preferably be formed from a material containing mutually different two resins.

In the case where the marker-forming layer 24 is formed from a material having the composition 2 mentioned above, the coating layer 25 is formed from a material containing mutually different two resins. One of them is miscible with the second resin mentioned above, preferably the second resin itself mentioned above. The other of them is miscible with the third resin mentioned above, preferably the third resin itself mentioned above. Thus, the guide wire 21 has reduced friction (or sliding resistance) and good adhesion (bonding) is achieved between the marker-forming layer 24 and the coating layer 25.

The coating layer 25 as a whole may contain one of the resins mentioned above in an amount of about 1 to 30 wt %, preferably about 3 to 20 wt %, and the coating layer 25 as a whole should contain the other of the resins mentioned above in an amount of about 80 to 97 wt %, so that good adhesion is achieved between the coating layer 25 and the marker-forming layer 24 as wells as the intermediate layer 28 and the guide wire 21 has reduced friction (or sliding resistance).

In the case where the marker-forming layer 24 is formed from a material having the composition 1 mentioned above or the composition 3 mentioned above, the coating layer 25 should preferably be formed from a material containing mutually different two resins. However, it may also be formed from a material containing only one resin.

In the case where the coating layer 25 is formed from a material containing only one resin, the resin should be miscible with the second resin mentioned above, or preferably the second resin itself, so that the guide wire 21 has reduced friction (or sliding resistance) and good adhesion (bonding) is achieved between the marker-forming layer 24 and the coating layer 25.

In the case where the coating layer 25 is formed from a material containing mutually different two resins, one of them should be miscible with the second resin mentioned above (preferably the second resin itself) and the other of them should be the fluororesin used in the second embodiment mentioned above, so that the guide wire 21 has reduced friction (or sliding resistance) and good adhesion (bonding) is achieved between the marker-forming layer 24 and the coating layer 25.

The content of each of the resins mentioned above is as mentioned above.

The intermediate layer 28 is formed from a material containing a first resin, a resin which is different from the first resin and miscible with the second resin mentioned above, and a pigment. Preferably, it is formed from a material containing a first resin, a second resin differing from the first resin, and a pigment. The pigment in this case should preferably be one which differs in color from that in the marker-forming layer 24.

The first resin may be a heat resistant resin having a melting point of 200° C. or higher, preferably about 200 to 300° C., like the one mentioned in the eighth embodiment. The first resin should be a thermosetting resin like the one mentioned in the eighth embodiment.

The color of the intermediate layer 28 depends mainly on the type and properties of the pigment contained therein, the composition and properties (particularly color tone) of the resin contained therein, and the amount of the pigment contained therein. Any color can be obtained by adjustment of these factors.

The intermediate layer 28 as a whole may contain the first resin in an amount of about 1 to 60 wt %, preferably about 3 to 30 wt %, so that good adhesion is achieved between the intermediate layer 28 and the undercoating layer 27.

Also, the intermediate layer 28 as a whole may contain the resin (e.g., the second resin) miscible with the second resin contained therein in an amount of about 1 to 30 wt %, preferably about 3 to 20 wt %, so that the marker-forming layer 24 firmly adheres to the intermediate layer 28 and the coating layer 25.

Also, the intermediate layer 28 as a whole may contain the pigment in an amount of about 10 to 98 wt %, preferably about 50 to 94 wt %, depending on the type and properties of the pigment therein and the composition of the resin therein, so that it takes on a desired color. The pigment in the intermediate layer 28 may be uniformly dispersed. However, it may exist locally in the outer surface of the intermediate layer 28.

The pigments may be used alone or in combination with one another.

The intermediate layer 28 may not contain the pigment. The thickness of the intermediate layer 28 is not specifically restricted; it should be about 1 to 20 μm, preferably about 2 to 10 μm.

The undercoating layer 27 is formed from a material containing a resin miscible with the first resin and a pigment, preferably from a material containing the first resin and a pigment. The pigment should preferably differ in color from the one contained in the marker-forming layer 24.

The color of the undercoating layer 27 depends mainly on the type and properties of the pigment contained therein, the composition and properties (particularly color tone) of the resin contained therein, and the amount of the pigment contained therein. Any color can be obtained by adjustment of these factors.

The undercoating layer 27 as a whole may contain the resin (e.g., the first resin) miscible with the first resin in an amount of about 1 to 90 wt %, preferably about 5 to 50 wt %, so that good adhesion is achieved between the undercoating layer 27 and the intermediate layer 28.

The content of the pigment in the undercoating layer 27 depends on the type and properties of the pigment and the composition and properties of the resin. For a desirable color, it is about 10 to 99 wt %, preferably about 50 to 95 wt %.

The pigment in the undercoating layer 27 may be uniformly dispersed. However, it may exist locally in the outer surface of the undercoating layer 27.

The pigments may be used alone or in combination with one another.

The undercoating layer 27 may not contain the pigment. The thickness of the undercoating layer 27 is not specifically restricted; it should be about 1 to 20 μm, preferably about 2 to 10 μm.

As mentioned above, the constituent material of the coating layer 25 and the constituent material of the marker-forming layer 24 contain mutually miscible resin (particularly the second resin in common), so that good adhesion is achieved between the marker-forming layer 24 and the coating layer 25.

Also, the constituent material of the marker-forming layer 24 and the constituent material of the intermediate layer 28 contain mutually miscible resin (particularly the second resin in common), so that good adhesion is achieved between the marker-forming layer 24 and the intermediate layer 28. Further, good adhesion is achieved between the coating layer 25 and the intermediate layer 28.

Also, the constituent material of the intermediate layer 28 and the constituent material of the undercoating layer 27 contain mutually miscible resin (particularly the first resin in common), so that good adhesion is achieved between the intermediate layer 28 and the undercoating layer 27.

This structure helps to prevent the individual layers from peeling off even when the guide wire 21 experiences bending and twisting repeatedly. The guide wire 21 thus obtained produces the same effect as the guide wire 21 obtained in the first embodiment mentioned above.

The advantage of the guide wire 21 is that the marker-forming layer 24, the undercoating layer 27, and the intermediate layer 28 take on any desired color in response to the kind, properties, and amount of the pigment contained therein or the composition of the resin material contained therein. This offers a wide selection of colors for the visible marker and the undercoating layer 7, thereby giving a combination of the highly visible marker-forming layer 24, the undercoating layer 27, and the intermediate layer 28 regardless of the color of the core wire 23 (or the member 22). Thus the resulting guide wire 21 has a highly visible marker.

The guide wire 21 may additionally have an outer layer.

The embodiments of the guide wire have been described in the context of the various illustrated embodiments. However, the present invention is not limited in this regard. The guide wires may be modified by replacing components with others having the same or similar functions, or by adding other components and processes.

The guide wire may have any two or more structures (features) in combination selected from the foregoing embodiments.

The guide wire should preferably be one which produces X-ray contrast images, so that it can be located in the living body. This object is achieved by adding a contrast medium (or a filler containing a contrast medium) to a desired position in the specific layer. The contrast medium is not specifically restricted so long as it gives X-ray contrast images; though it is preferably selected from metal powder or metal oxide powder.

The guide wire according to the present invention is not limited to one used in the context of inserting it into the lumen of an endoscope.

The principles, embodiments and modes of operation have been described in the foregoing specification, but the invention which is intended to be protected is not to be construed as limited to the particular embodiments disclosed. The embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A guide wire comprising:
 a member comprised of a core wire, said member possessing an outer surface;
 a bulge-forming layer arranged on the outer surface of the member;
 a coating layer covering the bulge-forming layer and the member at least in a region of the member at which the bulge-forming layer is arranged;
 said member, said bulge-forming layer and said coating layer defining a guide wire body, said guide wire body possessing an exterior surface, the bulge-forming layer resulting in spaced apart portions of the exterior surface of the guide wire body bulging outwardly relative to adjoining portions of the exterior surface of the guide wire body which are devoid of the bulge-forming layer and;
 wherein the bulge-forming layer is a color different from the member so as to enable endoscopic viewing by a user when the guide wire is internally disposed within a living body, the coating layer possessing transparency allowing a difference in color between the bulge-forming layer and the outer surface of the member to be visible through the coating layer so that the bulge-forming layer is a visible marker;
 wherein the coating layer is directly in contact with portions of the outer surface of the member which are devoid of the bulge-forming layer; and
 wherein the bulge-forming layer is comprised of a composite of a resin and a pigment.

2. The guide wire according to claim 1, wherein the portions of the outer surface of the member that are in contact with the coating layer possess surface irregularities.

3. The guide wire according to claim 1, wherein the outer surface of the member is the outer surface of the core wire.

4. The guide wire according to claim 1, wherein the core wire possesses a forward end and a rearward end, and both the bulge-forming layer and the coating layer extend from the forward end of the core wire to the rearward end of the core wire so that the core wire, the coating layer and the bulge-forming layer are longitudinally coextensive.

5. The guide wire according to claim 1, wherein the coating layer is comprised of a first resin, and the bulge-forming layer is comprised of the first resin.

6. A guide wire comprising:
 a member comprised of a core wire, the member possessing an outer surface;
 an undercoating layer arranged in contacting relation on the outer surface of the member, the undercoating layer possessing an outer surface;
 a bulge-forming layer arranged in contacting relation with the outer surface of the undercoating layer;
 a coating layer covering the bulge-forming layer,
 said member, said undercoating layer, said bulge-forming layer and said coating layer defining a guide wire body, the guide wire body possessing an exterior surface, the bulge-forming layer resulting in spaced apart portions of the exterior surface of the guide wire body bulging outwardly relative to adjoining portions of the exterior surface of the guide wire body which are devoid of the bulge-forming layer; and
 the bulge-forming layer and the undercoating layer being made of materials containing mutually miscible resins;

wherein the coating layer is directly in contact with portions of the outer surface of the undercoating layer which are devoid of the bulge-forming layer;

wherein the bulge-forming layer is comprised of a composite of mutually miscible resins and a pigment; and wherein the bulge-forming layer is configured so as to enable endoscopic viewing by a user when the guide wire is internally disposed within a living body.

7. The guide wire according to claim 6, wherein the bulge-forming layer and the undercoating layer are differently colored, the coating layer possessing transparency allowing the bulge-forming layer to be visible through the coating layer so that the bulge-forming layer is a visible marker.

8. The guide wire according to claim 6, wherein the coating layer directly adheres to the undercoating layer in regions devoid of the bulge-forming layer.

9. The guide wire according to claim 6, wherein the bulge-forming layer is a spiral configuration, a circular configuration, or a check pattern configuration.

10. The guide wire according to claim 6, wherein the coating layer is comprised of a first resin, and the bulge-forming layer is comprised of the first resin.

11. The guide wire according to claim 6, further comprising an outer layer covering the coating layer, the outer layer being comprised of a second resin, the coating layer being comprised of the second resin.

12. The guide wire according to Claim 6, wherein the bulge-forming layer is configured so as to enable endoscopic viewing by the naked eye of a user.

13. A guide wire comprising:

a member comprised of a core wire, the member possessing an outer surface;

a marker-forming layer at least partially encircling the outer surface of the member;

the marker-forming layer and the outer surface of the member both being colored by a pigment, the color of the outer surface of the member being different from the color of the marker-forming layer so as to enable endoscopic viewing by a user when the guide wire is internally disposed within a living body;

a coating layer covering the marker-forming layer;

the coating layer possessing transparency allowing the marker-forming layer to be visible through the coating layer so that the marker-forming layer serves as a visible marker; and wherein the member possesses spaced apart portions which are devoid of the marking-forming layer and the coating layer is directly in contact with portions of the outer surface of the member which are devoid of the marking-forming layer; and wherein the marker-forming layer is comprised of a composite of a resin and the pigment.

14. The guide wire according to claim 13, wherein the marker-forming layer is comprised of a first resin, a second resin differing from the first resin, and a pigment, and the coating layer is comprised of a material containing the second resin.

15. The guide wire according to claim 13, further comprising an outer layer covering the coating layer, the outer layer being transparent so that the marker-forming layer is visible through the outer layer as well as the coating layer, the outer layer and the coating layer being comprised of materials containing a common resin.

16. The guide wire according to claim 13, further comprising an undercoating layer covering the outer surface of the member and in contacting relation to the outer surface of the member, and an intermediate layer covering the undercoating layer so as to be located between the undercoating layer and the marker-forming layer, the marker-forming layer being in contacting relation on the intermediate layer, the intermediate layer being comprised of a material containing a first resin, and the undercoating layer being composed of a material containing a resin miscible with the first resin.

17. The guide wire according to in claim 13, wherein the marker-forming layer is comprised of a material containing a first resin, a second resin different from the first resin, and a pigment, and the coating layer being comprised of a material containing a resin which is different from first resin and miscible with the second resin.

18. The guide wire according to claim 13, further comprising an undercoating layer covering the outer surface of the core wire and in contacting relation to the outer surface of the core wire, the undercoating being comprised of a first resin and a first pigment, the marker-forming layer being comprised of a second pigment different from the first pigment, and a resin miscible with the first resin.

19. A method of fabricating a guide wire possessing an outermost surface comprising:

applying a resin material to a member comprising a core wire, the resin material comprising a first resin which is different in color from a material of the core wire;

removing portions of the resin material at spaced apart locations to expose the member at spaced apart locations so that remaining portions of the resin material at spaced apart locations form a bulge-forming layer having forward and rearward ends; and applying a second resin material possessing transparency to the bulge-forming layer and the member to directly contact the bulge-forming layer from the forward end of the bulge-forming layer to the rearward end of the bulge-forming layer and to directly contact the outermost surface of the member at the spaced apart locations devoid of the resin material so that an outermost surface of the member possesses spaced apart portions of the bulge-forming layer bulging outwardly relative to adjoining portions of the outermost surface of the member;

wherein the bulge-forming layer is configured so as to enable endoscopic viewing by a user when the guide wire is internally disposed within a living body.

20. The method according to claim 19, wherein the second resin material comprises a resin miscible with the first resin.

21. The method according to claim 19, wherein the second resin material applied to the first resin material forms a coating layer covering the bulge-forming layer, the second resin material comprising a pigment imparting a color to the coating layer, the first resin material also containing a pigment imparting a color to the bulge-forming layer different from the color of the coating layer.

22. The method according to claim 19, further comprising applying a resin material to the core wire to form the member comprised of the core wire and an undercoating layer, the resin material applied to the core wire comprising a resin miscible with the first resin, the second resin material comprising a resin miscible with a resin of the first resin material.

23. A method of fabricating a guide wire comprising:

applying a resin material to a member comprising a core wire, the resin material comprising a first resin containing a pigment which is different in color from a material of the core wire;

removing portions of the resin material at spaced apart locations to expose the member at spaced apart locations so that remaining portions of the resin material at spaced part locations form a colored marker-forming layer having forward and rearward ends;

applying a second resin material to the colored marker-forming layer and the member to form a coating layer directly contacting the marker-forming layer from the distal end of the marker-forming layer to the rearward end of the marker-forming layer and directly contacting an outermost surface of the member at the spaced apart locations devoid of the resin material;

the second resin material of the coating layer being transparent so that the colored marker-forming layer is visible through the coating layer;

wherein the marker-forming layer is configured so as to enable endoscopic viewing by a user when the guide wire is internally disposed within a living body.

24. The method according to claim 23, wherein the second resin material comprises a resin miscible with the first resin.

* * * * *